US012569443B2

(12) United States Patent
Meijerink et al.

(10) Patent No.: US 12,569,443 B2
(45) Date of Patent: *Mar. 10, 2026

(54) GASTRO-RETENTIVE DRUG DELIVERY SYSTEM

(71) Applicant: APeT Holding B.V., Ridderkerk (NL)

(72) Inventors: Hendrik Jan Cornelis Meijerink, Wespelaar (BE); Lekhram Changoer, IJsselstein (NL); Willem Blom, Berkel en Rodenrijs (NL); Marinella Regina Visser, Groningen (NL); Henderik Willem Frijlink, Groningen (NL); Anko Cornelus Eissens, Groningen (NL)

(73) Assignee: APeT Holding B.V., Ridderkerk (NL)

( * ) Notice: Subject to any disclaimer, the term of this patent is extended or adjusted under 35 U.S.C. 154(b) by 0 days.

This patent is subject to a terminal disclaimer.

(21) Appl. No.: 17/833,979

(22) Filed: Jun. 7, 2022

(65) Prior Publication Data

US 2023/0115025 A1 Apr. 13, 2023

Related U.S. Application Data

(63) Continuation of application No. 15/718,010, filed on Sep. 28, 2017, now abandoned, which is a
(Continued)

(51) Int. Cl.
*A61K 9/16* (2006.01)
*A61K 9/00* (2006.01)
(Continued)

(52) U.S. Cl.
CPC .......... *A61K 9/1652* (2013.01); *A61K 9/0065* (2013.01); *A61K 9/1635* (2013.01);
(Continued)

(58) Field of Classification Search
None
See application file for complete search history.

(56) References Cited

U.S. PATENT DOCUMENTS 3,976,764 A 8/1976 Watanabe et al.
4,973,467 A 11/1990 Sahley
(Continued)

FOREIGN PATENT DOCUMENTS

EP 2329810 A1 6/2011
WO 2010020098 A1 2/2010

OTHER PUBLICATIONS

Blom et al., "Neurologic Action of Megadoses of Vitamins", Bibithca Nutr Dieta (1986) No. 38, pp. 120-135.
(Continued)

*Primary Examiner* — Lakshmi S Channavajjala
(74) *Attorney, Agent, or Firm* — Ipsilon USA—NLO

(57) ABSTRACT

The invention relates to floating drug delivery systems (FDDS) that provide solutions to the particular problems often encountered with floating drug delivery systems described in the art. On such generally recognized problem is the vulnerability of the systems, especially damage to the gas-filled compartment making it accessible to water so as to impair its buoyancy, ultimately resulting in insufficient gastric residence time. The invention, in an aspect, provides a self-repairing FDDS that maintains its floating capacity after damaging. The floating drug delivery systems of the invention, furthermore, allow for incorporation of high loads of active ingredients. The floating drug delivery systems can be designed in such a way that release of active ingredient from the system occurs entirely independent from the pH of the fluid surrounding the system. Furthermore, the procedure of
(Continued)

manufacturing the floating drug delivery system of the invention is simple and straightforward, and therefore economically attractive.

13 Claims, 10 Drawing Sheets

Related U.S. Application Data continuation of application No. 14/415,114, filed as application No. PCT/NL2013/050538 on Jul. 15, 2013, now abandoned.

(51) Int. Cl.
| | | |
|---|---|---|
| *A61K 9/20* | (2006.01) | |
| *A61K 9/48* | (2006.01) | |
| *A61K 31/198* | (2006.01) | |
| *A61K 31/455* | (2006.01) | |
| *G01N 33/68* | (2006.01) | |

(52) U.S. Cl.
CPC .......... *A61K 9/1641* (2013.01); *A61K 9/1676* (2013.01); *A61K 9/2054* (2013.01); *A61K 9/4808* (2013.01); *A61K 9/4891* (2013.01); *A61K 31/198* (2013.01); *A61K 31/455* (2013.01); *G01N 33/6893* (2013.01); *Y10T 436/143333* (2015.01)

(56) References Cited

U.S. PATENT DOCUMENTS

| | | | | |
|---|---|---|---|---|
| 4,980,168 | A | 12/1990 | Sahley | |
| 5,057,323 | A | 10/1991 | Niwa et al. | |
| 5,648,095 | A | 7/1997 | Illum et al. | |
| 9,561,179 | B2 | 2/2017 | Castan et al. | |
| 10,881,614 | B2 * | 1/2021 | Meijerink ............ | A61K 9/4891 |
| 2007/0212411 | A1 | 9/2007 | Fawzy et al. | |
| 2009/0104171 | A1 | 4/2009 | Pardee et al. | |
| 2010/0015224 | A1 | 1/2010 | Singh et al. | |
| 2010/0285116 | A1 | 11/2010 | Joshi | |
| 2011/0027376 | A1 | 2/2011 | Boey et al. | |
| 2011/0171275 | A1 | 7/2011 | Jiang et al. | |
| 2014/0234409 | A1 | 8/2014 | Meijerink et al. | |
| 2018/0140553 | A1 | 5/2018 | Meijerink et al. | |

OTHER PUBLICATIONS

Welling, "Drug Toxicokinetics", Drug and Chemical Toxicology (1993) Marcel Dekker, Inc., (TOC only).

Araro, S. et al., "Floating drug delivery systems: A review", AAPS Pharmscitech. Springer New York LLC, US., vol. 6, No. 3, Oct. 19, 2005, pp. E372-E390.

Blom, W. et al. "Successful Nicotinamide treatment in an Autosomal Dominant Behavioral and Psychiatric Disorder", J, Inter. Metab. Dis., Suppl. 8, 1985, vol. 2, pp. 107-108.

Haslam, R. et al. "Effects of Megavitamin Therapy on Children with Attention Deficit Disorders", PEDIATRICS, Jul. 1984, vol. 74, No. 1. pp. 103-111.

Hoffer, A. "Vitamin B-3: Niacin and Its Amide", DOCTORYOURSELF. COM, 2011, 12 pgs.

Navab, F. et al. "Studies on intestinal absorption of amino acids and a dipeptide in a case of Hartnup disease", GUT, 1970, vol. 11, pp. 373-379.

Singh, B.N. et al., "Floating drug delivery systems: an approach to oral controlled drug delivery via gastric retention". Journal of Controlled Release, Elsevier, Amsterdam, NL, vol. 63, No. 3, Feb. 3, 2000, pp. 235-259.

Urine Indican Test (Obermeyer Test) Overview, Biohealth Diagnostics, Oct. 30, 2010, http://web.archive.org/web/20101030044926/http://biodia.com/general_content/indican_overview.html, 2 pgs.

Tang et al., "Sustained release of hydrophobie and hydrophilie drugs from a floating dosage form", International Journal of Pharmaceutics 336 (2007) 159-165, www.elsevier.com/locate/ijpharm.

Ghandforoush-Sattari et al., "Pharmacokinetics of Oral Taurine in Healthy Volunteers", SAGE-Hindawi Access to Research, Journal of Amino Acids, vol. 2010, Article ID 346237, 5 pages, doi:10.4061/2010/346237.

Stratford et al., "Nicotinamide pharmacokinetics in humans: effect of gastric acid inhibition, comparison of rectal vs oral administration and the use of saliva for drug monitoring", Britsh Journal of Cancer (1996) 74, 16-21.

Ellinger et al., "Tryptophan and the Biosynthesis of Nicotinamide", p. 276-281, Lister Institute of Preventive Medicine, London, S.W. 1, 1949.

Garten et al., "Nampt: Linking NAD biology, metabolism, and cancer", Trends Endocrinol Metab. Apr. 2009 ; 20(3): 130-138. doi:10.1016/j.tem.2008.10.004.

Hsu et al., "Nicotinamide phosphoribosyltransferase regulates cell survival through NAD+ synthesis in cardiac myocytes", Circ Res. Aug. 28, 2009; 105(5): 481-491. doi:10.1161/CIRCRESAHA.109. 203703.

Blom, "Intestinal Tryptophan Uptake, Transport and Metabolism", W. Blom, Ansynth Service BV.

Levina et al., "The influence of excipients on drug release from hydroxypropyl methylceullose matrices". Journal of Pharmaceutical Sciences, 93:11,2746-2754. (Year: 2004).

* cited by examiner

GASTRO-RETENTIVE DRUG DELIVERY SYSTEM

FIELD OF THE INVENTION

The invention relates to the fields of pharmacy and medicine. Among others, it relates to oral gastro-retentive drug delivery systems, in particular floating drug delivery systems, and the uses thereof in therapy.

BACKGROUND OF THE INVENTION

Oral administration of drugs is the most preferable way of drug delivery due to the simple and comfortable use and flexibility regarding dose strength and type of formulation. These factors may increase patient compliance. More than 50% of commercial drugs available in the market use oral administration for the delivery. During the last five decades, numerous oral delivery systems have been developed to act as a drug reservoir from which the active substance is released over an extended period of time and at controlled rate of release. However, there is evidence that in vivo drug release of solid oral controlled released dosage form is unpredictable despite its excellent in vitro release profile (Welling, P G 1993). Moreover, drug absorption profiles are often unsatisfactory in relation to the desired plasma profile and highly variable among individuals. One of the reasons for the unpredictable drug release, which causes variation in drug absorption among volunteers and patients, is associated with the transit time of the dosage form in the gastrointestinal tract (GIT). Gastric residence time (GRT) appears to be a major cause of overall transit time variability. First of all, the release of a drug from the delivery system may vary with the location of the drug in the GI-tract. If, for example, the drug release is pH dependent, significant differences in the release rate in the stomach and in the small intestine may exist. Secondly, the absorption of a drug may occur only in a limited part of the GI-tract. Once this part of the GI-tract is passed by the drug dosage form, drug release may occur in a reduced absorption or no absorption at all any longer. Since many drugs are absorbed in the proximal site of small intestine, GRT is an important variable that affects to a large extent oral drug absorption of controlled release dosage form. For drugs that are absorbed only in a limited part of the GI-tract, the limited residence time in the stomach and the upper small intestine, results in low oral bioavailability.

One of the options to reduce the variability in drug release and drug absorption and to increase the bioavailability of drugs from orally administered drug delivery systems, especially controlled release drug delivery systems, is to prolong the residence time of the dosage from in the stomach. Delivery systems that are intended for this purpose are often described as gastro-retentive dosage forms. Gastro-retentive dosage forms are delivery systems that will provide the system to be able to control the gastric residence time or gastric transit time of the dosage form to achieve a prolonged and predictable drug delivery profile in the upper part of the GI-tract. Controlling the residence time of drug delivery system in the stomach will control the overall gastrointestinal transit time since GRT appears to be the major causes of overall transit time variability, thereby resulting in an improved bioavailability of the drug.

The main objective in the development of gastro-retentive dosage forms is to overcome the clearance of gastric content that under normal circumstances occurs within 1-2 hours in the fasted stated by the housekeeping wave. Over the past three decades, the pursuit and exploration of devices designed to be retained in the upper part of the gastrointestinal (GI) tract has advanced consistently in terms of technology and diversity. Gastric retention will provide advantages such as the delivery of drugs with a limited absorption window to those parts of the intestinal tract where absorption (with a slow release profile). Also, a longer residence time in the stomach could be advantageous for local action in the stomach or the upper part of the small intestine, for example treatment of peptic ulcer disease, or eradication of *Helicobacter pylori*. Furthermore, improved bioavailability is expected for drugs that are absorbed preferentially from the upper part of the GI-tract such as the duodenum. These drugs can be delivered ideally by slow release from the stomach. Many drugs categorised as once-a-day delivery have been demonstrated to have suboptimal absorption due to dependence on the gastro-intestinal transit time of the dosage form, making traditional extended release development challenging. Therefore, a system designed for longer gastric retention will extend the time during which drug absorption can occur in for example the upper small intestine.

Various approaches have been followed to encourage gastric retention of an oral dosage form. Floating systems have low bulk density so that they can float on the gastric juice in the stomach. For reviews on floating drug delivery systems, see Singh et al. (2000; J. Contr. Rel. 63, 235-259) and Arora et al. (2005, AAPS PharmSciTech; 6(3) E372-E390) and references cited therein. Briefly, gastro-retentive systems can be based on the following concepts:

A) buoyant (floating) systems: these are systems that have a density lower that that of the gastric fluids so that they remain floating in the stomach. These systems can be subdivided in:

A1) low-density systems have a density lower than that of the gastric fluid so they are buoyant;

A2) hydrodynamically balanced systems (HBS)—incorporated buoyant materials enable the device to float;

A3) effervescent systems—gas-generating materials such as carbonates are incorporated. These materials react with gastric acid and produce carbon dioxide (gas), which allows them to float; The system contains means, such as a coating, to keep the gas for some time in the delivery system.

A4) raft systems incorporate gels such as alginate or HPMC gels—these have a carbonate component and, upon reaction with gastric acid, bubbles form in the gel, enabling floating;

B) bioadhesive or mucoadhesive systems—these systems permit a given drug delivery system to be incorporated with bio/mucoadhesive agents, enabling the device to adhere to the stomach (or other GI) walls, thus resisting gastric emptying.

C) systems that have a size or will expand in the stomach to a size that is too large to pass the pyloric sphincter.

A number of major drug companies have focused efforts on the design of gastric retention technologies. For instance, Alza Corporation has developed a gastro-retentive platform for the OROS® system, which showed prolonged gastric residence time in a dog model as the product remained in the canine stomach at 12 hours post dose and was frequently present at 24 hours. In humans, in the fasted state, the average gastric residence time for the same system was 33 minutes. DepoMed, Inc. has developed technology that consists of a swellable tablet. After ingestion of the tablet, it swells and achieves sufficient size to resist gastric emptying, while simultaneously providing controlled release of the drug. Two of the products that DepoMed is developing include Metformin GR™ and Ciprofloxacin GR™. Pfizer Pharmaceuticals has patents for gastric retention technology that uses extendable arms. Merck & Co., Inc., has patents describing technologies using various unfolding shapes to encourage gastric retention. Madopar® is an HBS floating system containing 200 mg levodopa and 50 mg benserazide. The formulation consists of a capsule designed to float on the stomach contents. Following dissolution of the gelatin shell, a matrix body is formed consisting of the active drug and other substances.

A major disadvantage of many of the systems described above is that they require special production technologies and/or specific machinery. For example, tabletting machines able to produce multi-layer tablets are necessary to produce swellable multi-layer tablets. A floating system patented by Eisa Co. Ltd. had the problem of incorporating the drug (see Singh et al. (2000; J. Contr. Rel. 63, 235-259). The production of systems using effervescence has limitations regarding the use of aqueous liquids and the systems containing effervescence couples require special (e.g. moisture protecting) packaging. The production of systems with a special shape requires special compaction or moulding tools. Many systems may suffer from limitations in dose strength; swellable systems may for example require large fractions of polymers in the system. Many of the excipients (such as the polymers used) may not have been tested as safe excipients yet or they may be rather expensive. Furthermore, many of the systems may have a high cost of production because of the combination of specially adapted machinery and expensive excipients they require. Finally, many systems suffer from the fact that they are rather fragile and their gastro-retentive performance may be seriously compromised in case of damage of the dosage form, e.g. a fissure or crack in a coating layer, an edge broken from a tablet or inactivation of the effervescent system by moisture.

The above developments highlight the continuous need and industrial interest for developing new gastric retention formulations that can readily be developed, tested and manufactured. In view of this ongoing need, the present inventors set out to provide an alternative gastro-retentive dosage form. They aimed in particular at the development of an economically attractive oral drug delivery system allowing for the controlled and prolonged gastric residence of solid drug dosage forms, which would readily be accepted by registration authorities and that was able to provide controlled release of the drug(s) over periods between 1.5 and 24 hour after administration. One further goal was to provide a floating system that is simple and relatively cheap to manufacture. Yet a further goal was to provide a system that is physically robust and/or does not loose its gastro-retentive properties upon minor damage.

BRIEF DESCRIPTION OF THE DRAWINGS

In the drawings, like reference characters generally refer to the same parts throughout the different views. The drawings are not necessarily to scale, emphasis instead generally being placed upon illustrating the exemplary principles of the disclosure. In the following description, the disclosure may be described with reference to the following drawings, in which.

SUMMARY OF THE INVENTION

Figure 1:
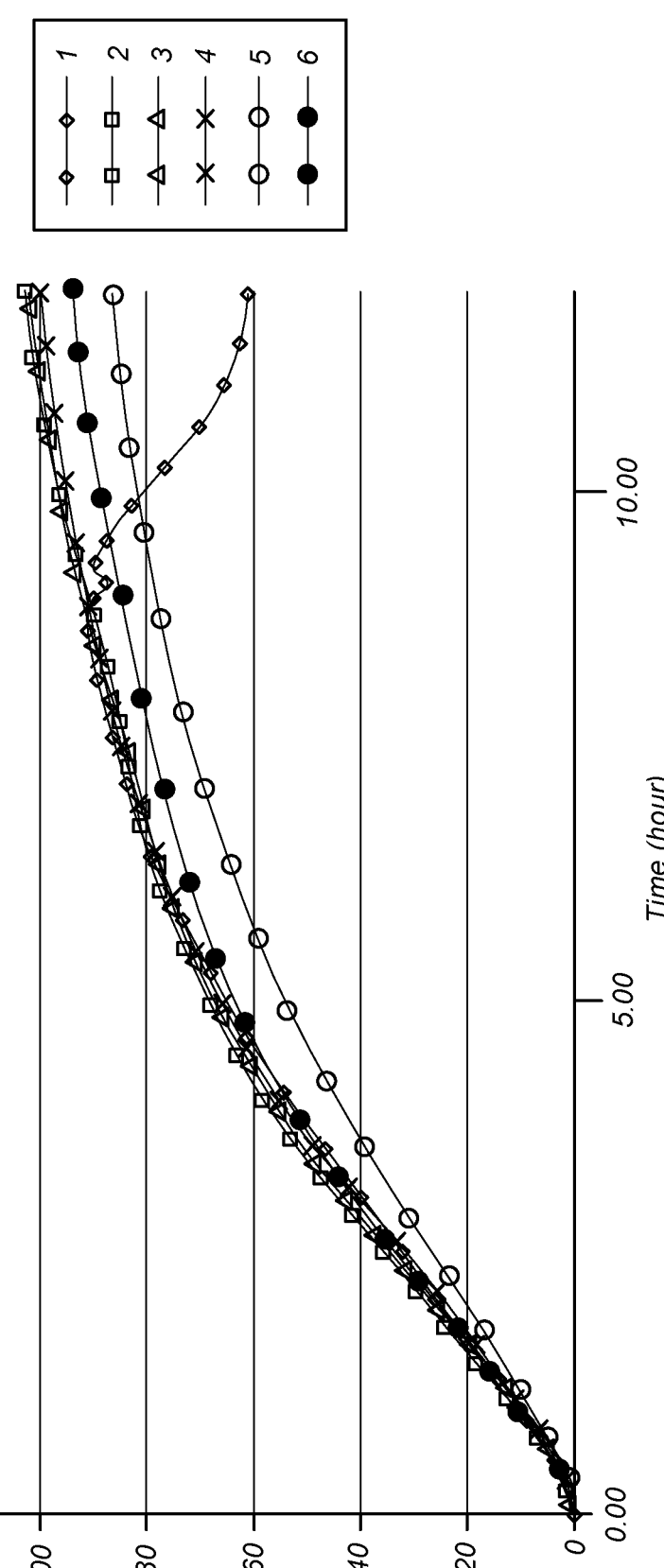
FIG. 1 illustrates a release profile of the 300 mg FDDS.

It was surprisingly found that at least some of these goals could be met by the provision of a floating drug delivery system (FDDS), comprising a particle having a hollow, gas-filled core bordered by a wall of at least one aqueous soluble, erodible, disintegrating or degradable material, typically a polymer, said wall being surrounded by a coating comprising at least one active ingredient.

The present invention, in an aspect, provides a solution to the particular problems encountered with many drugs that are absorbed (only/mainly) in the proximal site of small intestine The formulations facilitate absorption of active ingredient into the systemic circulation from only a limited part of the (proximal) intestinal tract for an extended period of time after administration, by enhancing the gastro-retention or gastric residence time of the delivery system, while continuously releasing active ingredient from the system.

Surprisingly, the present inventors established that, at least in some cases, the use of oral long acting formulations of the invention allows for effective and treatments, not only with fewer dosages per day, but also with total daily dosages significantly below those suggested in the art.

In a particularly preferred embodiment of the invention, the floating drug delivery system (FDDS) comprises a coating containing a polymer that swells upon contact with water. An FDDS according to this embodiment has the advantage that it can maintain its buoyancy even when (severely) damaged. The vulnerability of floating drug delivery systems is a generally recognized problem. Damaging of the drug delivery system, such as is often encountered during production, transportation and, especially, during ingestion (e.g. as a result of inadvertent chewing motions by the subject taking the formulation), may easily make the gas-filled compartment accessible to water so as to impair its buoyancy, ultimately resulting in insufficient gastric residence time. A solution to this problem is provided by the present invention, as will be illustrated in the appended examples.

The floating drug delivery systems of the invention, contrary to many floating dosage forms described in the art, allow for incorporation of high loads of active ingredients, as will be apparent from the examples.

It has also been established that, in accordance with the invention, floating drug delivery systems can be developed wherein release of active ingredient from the system occurs entirely independent from the pH of the fluid surrounding the system.

Furthermore, in contrast to (multi)particulate floating dosage forms, the procedure of manufacturing the floating drug delivery system of the invention is simple and straight-forward, and therefore economically attractive, in particular when the particle is filled with air.

These and other aspects of the invention and its preferred embodiments will be described in more detail and exemplified in the following sections.

DETAILED DESCRIPTION OF THE INVENTION

A first aspect of the invention concerns a floating drug delivery system (FDDS), comprising a particle having a hollow, gas-filled core bordered by a wall of at least one aqueous soluble, erodible, disintegrating or degradable material, said wall being surrounded by a coating comprising at least one active ingredient.

A particularly preferred embodiment of the invention, a floating drug delivery system (FDDS) is provided, comprising a particle having a hollow, gas-filled core bordered by a wall of at least one aqueous soluble, erodible, disintegrating or degradable polymer, said wall being surrounded by a coating comprising at least one active ingredient.

In one embodiment, the invention provides a FDDS comprising a capsule having a hollow, gas-filled core bordered by a wall of at least one aqueous soluble, erodible, disintegrating or degradable polymer, said wall being surrounded by a coating comprising at least one active ingredient.

It will be understood that essentially any type of active ingredient can be incorporated in the coating. The expression 'active ingredient' refers to any compound having biological activity, or being capable of being converted to such compound (e.g. a pro-drug). In embodiments of this inventions the term 'active ingredient' is synonymous for and interchangeable with the terms 'pharmacologically active ingredient', 'pharmaceutically active ingredient', 'therapeutically acceptable ingredient', 'drug', etc. In embodiments of this invention, the term 'active ingredient' also encompasses micronutrients, neutraceuticals, food supplements, probiotics, prebiotics, etc.

Examples of (pharmacologically/pharmaceutically) active ingredients that can benefit from using gastro-retentive drug delivery devices include drugs acting locally in the stomach; drugs that are primarily absorbed in the stomach or, in particular, in the upper intestinal tract; drugs that are poorly soluble at an alkaline pH; drugs with a narrow window of absorption; drugs absorbed rapidly from the GI tract; drugs that are absorbed only or mainly in the proximal site of small intestine and/or drugs that degrade in the lower intestinal tract or colon. It may be a material selected from the group consisting of AIDS adjunct agents, alcohol abuse preparations, Alzheimer's disease management agents, amyotrophic lateral sclerosis therapeutic agents, analgesics, anesthetics, antacids, antiarythmics, antibiotics, anticonvulsants, antidepressants, antidiabetic agents, antiemetics, antidotes, antifibrosis therapeutic agents, antifungals, antihistamines, antihypertensives, anti-infective agents, antimicrobial s, antineoplastics, antipsychotics, antiparkinsonian agents, antirheumatic agents, appetite stimulants, appetite suppressants, biological response modifiers, biologicals, blood modifiers, bone metabolism regulators, cardioprotective agents, cardiovascular agents, central nervous system stimulants, cholinesterase inhibitors, contraceptives, cystic fibrosis management agents, deodorants, diagnostics, dietary supplements, diuretics, dopamine receptor agonists, endometriosis management agents, enzymes, erectile dysfunction therapeutics, fatty acids, gastrointestinal agents, Gaucher's disease management agents, gout preparations, homeopathic remedy, hormones, hypercalcemia management agents, hypnotics, hypocalcemia management agents, immunomodulators, immunosuppressives, ion exchange resins, levocarnitine deficiency management agents, mast cell stabilizers, migraine preparations, motion sickness products, multiple sclerosis management agents, muscle relaxants, narcotic detoxification agents, narcotics, nucleoside analogs, non-steroidal anti-inflammatory drugs, obesity management agents, osteoporosis preparations, oxytocins, parasympatholytics, parasympathomimetics, phosphate binders, porphyria agents, psychotherapeutic agents, radioopaque agents, psychotropics, sclerosing agents, sedatives, sickle cell anemia management agents, smoking cessation aids, steroids, stimulants, sympatholytics, sympathomimetics, Tourette's syndrome agents, tremor preparations, urinary tract agents, vaginal preparations, vasodilators, vertigo agents, weight loss agents, Wilson's disease management agents, and mixtures thereof.

Examples of active ingredients that may be particularly suitable for incorporation in the FDDS of the invention inlcude acetaminophen, acetylsalicylic acid, acyclovir, amoxycillin, ampicillin, aspirin, atenolol, baclofen, benserazide, bifosfonaten (alendronate), captopril, carbidopa, chlordiazepoxide, chlordiazepoxide, chlorpheniramine, cinnarizine, ciprofloxacin, cisapride, diazepam, diclofenac, diltiazem, florouracil, furosemide, gabapentin, ganciclovir, G-CSF, glipizide, griseofulvin, iboprufen, ijzer zouten, indomathacin, isosorbide, ketoprofen, levodopa, melatonin, metformine, minocyclin, misoprostol, nicardipine, nimodipine, p-aminobenzoic acid, pentoxyfillin, piretanide, p-nitroaniline, prednisolone, propranlol, quinidine gluconate, riboflavin, riboflavin-5'-Phosphate, sotalol, terfenadine, tetracycline, theophylline, tranilast, urodeoxycholic acid, ursodeoxycholic acid, verapamil and vitamin E.

In an embodiment of the invention, the active ingredient is levodopa, or a salt ester, derivative, hydrate and/or solvate thereof. Levodopa is the INN name for L-3,4-dihydrophenylalanine. In an embodiment of the invention the active ingredient is a dopamine precursor or a catecholamine precursor. In an embodiment of the invention the active ingredient is a dopamine agonist. In an embodiment of the invention the active ingredient is a combination of levodopa and carbidopa.

In an embodiment of the invention, the active ingredient is nicotinamide. Nicotinamide (IUPAC name pyridine-3-carboxamide), also known as niacinamide and nicotinic acid amide, is the amide of nicotinic acid (vitamin B3/niacin). It will be understood by the skilled reader that nicotinamide, as well as other compounds used in the present invention, may be capable of forming salts, complexes, hydrates and solvates, and that the use of such forms in the defined treatments is contemplated herein.

In a preferred embodiment, the active ingredient is not nicotinamide. In a preferred embodiment the active ingredient is not nicotinamide or a salt, a complex, a hydrate or a solvate thereof. An embodiment of the invention concerns a floating drug delivery system (FDDS), comprising a particle, preferably a capsule, having a hollow, gas-filled core bordered by a wall of at least one aqueous soluble, erodible, disintegrating or degradable polymer, said wall being surrounded by a coating comprising at least one active ingredient, wherein said coating comprises a polymer that swells upon contact with water, with the exception of a floating drug delivery system (FDDS), comprising a particle having a hollow, gas-filled core bordered by a wall of at least one aqueous soluble, erodible, disintegrating or degradable polymer, said wall being surrounded by a coating comprising nicotinamide.

In a preferred embodiment a floating drug delivery system is provided that, upon administration to a subject to be treated, is capable of remaining in the stomach for a period extending over at least 2, at least 3, at least 4, at least 5 or at least 6 hours, typically in the fasted state. In an embodiment the FDDS is capable of remaining in the stomach for a period extending over at least 12 or at least 24 hours, typically in the fasted state. Furthermore, in a preferred embodiment of the invention an FDDS is provided that, upon administration to a subject to be treated, is capable of releasing active ingredient to the GIT (stomach and proximal small intestine) for a period extending over at least 2, at least 3, at least 4, at least 5 or at least 6 hours, typically in the fasted state. In an embodiment the FDDS is capable of releasing active ingredient to the GIT for a period extending over at least 12 or at least 24 hours, typically in the fasted state. Furthermore, in a preferred embodiment of the invention an FDDS is provided that, in a standard in vitro test in a so called USP dissolution apparatus, is capable of releasing active ingredient from the delivery system in a so called slow release profile. Such a release profile is preferably characterized by a release of less than 45% of the total active ingredient content after 1 hour and/or the release of more than 30% and less than 75% after 3 hours and/or the release of less than 80% after 6 hours. In an alternative embodiment the release profile is characterized by the release of less than 35% of the total active ingredient content after 1 hour and/or the release of more than 30% and less than 75% after 5 hours and/or the release of more than 80% of the total active ingredient content after 10 hours. In an alternative embodiment the release profile is characterized by the release of less than 25% of the total active ingredient content after 1 hour and/or the release of more than 30% and less than 75% after 12 hours and/or the release of more than 80% of the total active ingredient content after 24 hours.

Unless specified otherwise in this document, in vitro testing of the FDDS system is carried out in a so called USP dissolution apparatus II. With the dissolution medium (500 to 900 ml) at a temperature of 37° C. and a rotational speed of the paddle of 50 tot 75 RPM. For investigating the release profile or floating capacity of the gastro-retentive systems, simulated gastric fluid of the following composition is used: sodium lauryl sulphate 2.5 g; sodium chloride 2.0 g; 0.01-0.05 N hydrochloric acid in water 1000 ml. Active ingredient concentrations in the dissolution medium can be determined by any suitable analytical method, like ultraviolet absorption or HPLC analysis.

In a preferred embodiment of the invention an FDDS is provided, which remains buoyant on the gastric fluid upon administration, typically to achieve the afore-defined goals. Usually the buoyancy is characterized by the floating time (h) and/or buoyancy AUC (mg h). In a preferred embodiment of the invention a floating delivery system is provided having a floating time of at least 2, at least 3, at least 4, at least 5 or at least 6 hours when tested in vitro in the USP dissolution apparatus II. In an embodiment an FDDS is provided having a floating time of at least 12 or at least 24 hours when tested in vitro in the USP dissolution apparatus II.

Preferably, in the FDDS of the invention, active ingredient is present in a coating that encompasses or surrounds a solid particle made of at least one aqueous soluble, erodible, disintegrating or degradable polymer (e.g. by coating onto the surface of the particle), said particle having a hollow, gas-filled core bordered by a wall of at least one degradable polymer. As will be understood, the gas is a non-toxic gas. Air is the preferred gas. Because of the gas-filled compartment, lacking any particulate matter or matrix components, an FDDS provided herein having unique floating capacity and therefore very good gastric retention properties. Using an established in vitro gastric fluid simulation system, a floating time of at least up to 24 hours was observed. Thus, provided herein is gastric retention device capable of remaining in the stomach for at least 6, preferably at least 9, more preferably at least 12 hours. Also provided is the use of an air-filled capsule, generally lacking any therapeutically active ingredient, as a floating carrier for a drug in a gastro-retentive drug formulation.

According to the invention, the active ingredient is present in an outer layer or coating that controls not only the penetration of liquid (e.g. gastric fluid) into the particle, but also the release of active ingredient from the particle. Thus, in contrast to floating systems known in the art comprising (sub)compartments or chambers filled with air, such as floating microspheres, the present invention is conceptually different in that the active ingredient is present on the exterior of the gas filled compartment, and essentially absent (at least upon manufacture) from the inner core of a particle.

As will be explained below, the particle may be a conventional gelatin or HPMC capsule known in the art, which is easily provided with a coating comprising active ingredient. The system can be produced using only excipients that are known to be safe for human or animal use and that are accepted by regulatory authorities.

Typically, the particle in the FDDS of the invention itself will lack any therapeutically active ingredient and only contains active ingredient in the external coating layer. However, it is also encompassed that a small (e.g. up to about 50%, preferably up to 35% or 30%, more preferably up to 20%, like 5, 10, 12, 15 or 17%) volume of the capsule or other type of hollow particle is filled with active ingredient, or another active ingredient, as long as the overall density of the capsule remains sufficiently low to allow for floating. Therefore, also provided is the use of a capsule of which only 50% or less, preferred is 35% or less even more preferred 20% or less, of the volume is filled with active ingredient or another active ingredient and the remaining volume is gas-filled as floating carrier for a drug in a gastro-retentive drug formulation. Only when the capsule erodes or disintegrates, its content is released. This may for instance be advantageous for applications wherein it is desirable to provide a final "burst" dose of the drug at the end of the release period. For example, a FDDS comprising the majority of active ingredient in the particle coating and a minor fraction within the coated particle allows achieving low yet sustained blood drug levels during the night, followed by an increased drug level in the morning. This is especially advantageous for the treatment of diseases wherein symptoms are worse in the morning, such as rheumatoid arthritis (RA) or asthma.

To protect the stomach lining to continued exposure of certain active ingredients, an embodiment is envisaged wherein the FDDS contains the active ingredient in microencapsulate form, which microencapsulates are dispersed within the external coating layer of the FDDS. The microencapsulate typically contains a core comprising or consisting of active ingredient covered by a layer of enteric polymer, designed to dissolve upon entry of the released microcapsules from the stomach into the small intestine. Alternatively the microencapsulate may simply comprise particles containing active ingredient dispersed within an enteric polymer matrix, designed to dissolve upon entry of the released microencapsulate from the stomach into the small intestine.

The skilled person will be able to select the appropriate materials to obtain a coating, and optionally a microrencapsulate for incorporation in said coating, yielding the desired characteristics with respect to liquid penetration and the release of the active ingredient in accordance with the afore described embodiments.

In a preferred embodiment of the invention, an FDDS as defined herein is provided, comprising a coating layer containing active ingredient in an amount of at least 40 wt. %, at least 50 wt. %, at least 60 wt. %, at least 70 wt. %, at least 75 wt. %, or at least 80 wt. %, based on the total weight of said coating layer, of active ingredient.

The active ingredient may be present in two or more layers of the coating, each layer having a distinct composition. It is also possible to provide the particle with a "subcoating" and/or "topcoating" to achieve a desired GRT and/or release profile. A single coating layer comprising active ingredient may be preferable in some embodiments for reasons of simplicity. However, in other preferred embodiments several layers of coatings may be applied, typically having distinct compositions and active ingredient amounts. As will be shown in the examples, the use of two or three coating layers having distinct release profiles allows for the design of formulations capable of near constant active ingredient release over periods of up to 12 hours. In one such embodiment an FDDS is provided comprising three coating layers, wherein the inner layer comprises 50-90 wt %, 60-87 wt % or 70-85 wt % of active ingredient, based on the total weight of the inner coating layer; the middle layer comprises 30-70 wt %, 40-60 wt % or 45-55 wt % of active ingredient, based on the total weight of the middle coating layer; and the outer layer comprises less than 10 wt %, less than 5 wt % or less than 1 wt % of active ingredient based on the total weight of the outer coating. In another embodiment an FDDS is provided comprising two coating layers, wherein the inner layer comprises 50-90 wt %, 60-87 wt % or 70-85 wt % of active ingredient, based on the total weight of the inner coating layer; and the outer layer comprises less than 10 wt %, less than 5 wt % or less than 1 wt % of active ingredient based on the total weight of the outer coating layer.

The coating materials of the one or more coating layers may be selected from the group consisting of coating materials resistant to gastric juice, release-controlling polymers, and mixtures thereof. Release-controlling polymers are well known in the art of drug formulations for controlled (e.g. sustained) release, and include swellable polymers, or polymers that are poorly water-soluble or water-insoluble. Exemplary release controlling polymers are hydrophilic cellulose derivatives (such as HPMC, HPC, MC, HEC, CMC, sodium-CMC), PVP, PVA, Carboxyvinyl polymer (Carbomer), Poly(ethyleneoxide) (Polyox WSR), alginates, pectins, guar gum, vinylpyrrolidone-vinyl acetate copolymer, dextrans, carrageenan, gellan, hyaluronic acid, pullulan, scleroglucan, xanthan, xyloglucan, chitosan, poly(hydroxyethyl methacrylate), ammoniomethacrylate copolymers (such as Eudragit RL or Eudragit RS), Poly (ethylacrylate-methylmetacrylate) (Eudragit NE), and Ethylcellulose. The coating may comprise a mixture of at least two release controlling polymers. For instance, a combination of HPMC and Eudragit RL was found to be very useful. Eudragit RL PO is a polymer for controlled release drug formulation. Due to the insolubility in the acid fluids of the stomach it is able to give a release of active ingredients over the desired period of time.

In another preferred embodiment, the invention provides a floating drug delivery system comprising a particle having a hollow, gas-filled core bordered by a wall, as defined herein, and comprising one or more coating layers comprising a combination of HPMC and starch as coating material, typically in a ratio within the range of 8:1-1:1, preferably 6:1-2:1, more preferably 5:1-3:1, most preferably about 4:1. The use of hypromellose was found to favourably delay active ingredient release.

In a particularly preferred embodiment of the present invention, said starch is pregelatinized starch.

In another preferred embodiment, the invention provides a floating drug delivery system comprising a particle having a hollow, gas-filled core bordered by a wall comprising one or more coating layers comprising a combination of HPMC and pregelatinized starch as coating material, typically in a ratio within the range of 1:1-1:8, preferably 1:1-1:6, more preferably 1:1-1:5, most preferably 1:1-1:4. As will be evident from the appending examples, the combination of hypromellose and pregelatinized starch is very advantageous in that it allows for accurate programming of active ingredient release, depending on the choice and nature of the active ingredient.

In preferred embodiments of the invention, an FDDS is provided comprising at least two active ingredient containing coating layers, e.g. as described here above, having distinct ratios of hypromellose and starch, the outer layer typically comprising a larger amount of hypromellose, relative to starch, than the inner layer.

In a particularly preferred embodiment of the present invention, said starch is pregelatinized starch.

In another preferred embodiments of the invention, an FDDS is provided comprising an active ingredient containing inner coating layer, e.g. as described here above, as well as an outer coating layer that does not contain active ingredient. The use of an outer coating layer allows for accurate programming of active ingredient release, as will be illustrated in the appended examples. In an embodiment, the inner and outer coating layers comprise hypromellose and pregelatinized starch. The inner and outer layer may comprise hypromellose and pregelatinized starch in the same (relative) amounts. In an embodiment the outer layer typically comprises a larger amount of hypromellose, relative to pregelatinized starch, than the inner layer.

Furthermore, it has been established that coating layers comprising hypromellose or other water-swellable polymers maintained their favourable release profile and floating properties when mechanically damaged or even ruptured, as will be illustrated in the examples here below.

Finally, it was established that the FDDS produced with these compositions was physically strong and robust, with crushing strengths far over 100 N. Hence, in an embodiment of the invention, an FDDS as defined herein is provided having a crushing-strength of at least 100 N, more preferably of at least 150 N.

Hence, a preferred embodiment of the invention concerns the FDDS as defined herein, and its use, wherein a polymer is used that swells upon contact with water, so as to render the FDDS 'self-repairing'. Most preferably said water-swellable polymer is hypromellose. In an embodiment of the invention, said water-swellable polymer is not hypromellose.

A particularly preferred embodiment of the invention concerns a floating drug delivery system (FDDS), comprising a particle, preferably a capsule, having a hollow, gas-filled core bordered by a wall of at least one aqueous soluble, erodible, disintegrating or degradable polymer, said wall being surrounded by a coating comprising at least one active ingredient, wherein said coating comprises a polymer that swells upon contact with water.

Another preferred embodiment of the invention concerns a floating drug delivery system (FDDS), comprising a particle, preferably a capsule, having a hollow, gas-filled core bordered by a wall of at least one aqueous soluble, erodible, disintegrating or degradable polymer, said wall being surrounded by a coating comprising at least one active ingredient, wherein said coating comprises hypromellose or another water-swellable polymer.

Another preferred embodiment of the invention concerns a floating drug delivery system (FDDS), comprising a particle, preferably a capsule, having a hollow, gas-filled core bordered by a wall of at least one aqueous soluble, erodible, disintegrating or degradable polymer, said wall being surrounded by a coating comprising at least one active ingredient, wherein said floating drug delivery system maintains its release profile and floating properties when mechanically damaged or ruptured Another preferred embodiment of the invention concerns a floating drug delivery system (FDDS), comprising a particle, preferably a capsule, having a hollow, gas-filled core bordered by a wall of at least one aqueous soluble, erodible, disintegrating or degradable polymer, said wall being surrounded by a coating comprising at least one active ingredient, wherein a polymer is used that swells upon contact with water, so as to render the FDDS self-repairing.

Another preferred embodiment of the invention concerns a floating drug delivery system (FDDS), comprising a particle, preferably a capsule, having a hollow, gas-filled core bordered by a wall of at least one aqueous soluble, erodible, disintegrating or degradable polymer, said wall being surrounded by a coating comprising at least one active ingredient, wherein said coating comprises a water-swellable polymer other than hypromellose.

Another preferred embodiment of the invention concerns a floating drug delivery system (FDDS), comprising a particle, preferably a capsule, having a hollow, gas-filled core bordered by a wall of at least one aqueous soluble, erodible, disintegrating or degradable polymer, said wall being surrounded by a coating comprising at least one active ingredient, wherein said coating comprises a waterswellable polymer is not hypromellose.

Typically, by "water swellable polymer" is meant a polymer that does not readily dissolve in water (or does not dissolve in water at all) but interacts with water to cause the polymer to increase in volume. Water swellable polymers useful in the preparation of the FDDS of this invention include polymers that are non-toxic and that swell in a dimensionally unrestricted manner upon imbibition of water and hence of gastric fluid. Examples of polymers meeting this description are: cellulose polymers and their derivatives including, but not limited to, hydroxymethyl cellulose, hydroxyethyl cellulose, hydroxypropyl cellulose, hydroxypropylmethyl cellulose, and carboxymethylcellulose; polysaccharides and their derivatives; polyalkylene oxides; polyethylene glycols; chitosan; poly(vinyl alcohol); xanthan gum; maleic anhydride copolymers; poly(vinyl pyrrolidone); starch, in particular pregelatinized starch, and starch-based polymers; carbomer; maltodextrins; amylomaltodextrins, dextrans, poly (2-ethyl-2-oxazoline); poly (ethyleneimine); polyurethane hydrogels; and crosslinked polyacrylic acids and their derivatives. Further examples are copolymers of the polymers listed above, including block copolymers and graft polymers. Specific examples of copolymers are PLURONICR®, and TECTONICS®, which are polyethylene oxide-polypropylene oxide block copolymers available commercially. Further examples are hydrolyzed starch polyacrylonitrile graft copolymers.

In a particularly preferred embodiment of the invention concerns a floating drug delivery system (FDDS), comprising a particle, preferably a capsule, having a hollow, gas-filled core bordered by a wall of at least one aqueous soluble, erodible, disintegrating or degradable polymer, said wall being surrounded by a coating comprising at least one active ingredient, wherein said coating comprises a polymer selected from the group consisting of hydrophilic cellulose derivatives, such as HPMC, HPC, MC, HEC, CMC, sodium-CMC); PVP; PVA; carboxyvinyl polymer (carbomer); poly (ethyleneoxide) (polyox WSR), alginates, pectins, guar gum, vinylpyrrolidone-vinyl acetate compolymer; dextrans; carrageenan; gellan; hyaluronic acid; pullulan; scleroglucan; xanthan; xyloglucan.

In a preferred embodiment of the invention, an FDDS as defined herein is provided, wherein at least 50 wt. %, at least 60 wt. %, at least 70 wt. %, at least 75 wt. %, at least 80 wt. %, at least 85 wt. %, at least 90 wt. % or at least 95 wt. % of the coating excipients, i.e. of the materials contained in the coating other than the active ingredient(s), is a water-swellable polymer as defined in the foregoing.

The FDDS coating may also comprise one or more enteric polymer coating materials. The term "enteric polymer" is a term of the art referring to a polymer which is preferentially soluble in the less acid environment of the intestine relative to the more acid environment of the stomach. Useful enteric polymers for practising the present invention include cellulose acetate phthalate, cellulose acetate succinate, methylcellulose phthalate, ethylhydroxycellulose phthalate, polyvinylacetatephthalate, polyvinylbutyrate acetate, vinyl acetate-maleic anhydride copolymer, styrene-maleic monoester copolymer, methacrylic acid methylmethacrylate copolymer, methyl acrylate-methacrylic acid copolymer, methacrylate-methacrylic acid-octyl acrylate copolymer, and combinations thereof.

In a specific aspect, the invention provides a delivery system comprising a particle having a hollow, gas-filled core bordered by a wall of at least one aqueous soluble, erodible, disintegrating or degradable material, typically a polymer, said wall being surrounded by a coating comprising at least one enteric polymer and active ingredient, preferably wherein the enteric polymer is a pharmaceutically acceptable methacrylic acid methylmethacrylate copolymer, such as a polymer sold under the trade name Eudragit™, including polymers from the Eudragit RL or Eudragit RS series. Again, mixtures of different types of coating polymers may be used. In one embodiment, the coating comprises a mixture of an enteric polymer, such as Eudragit RL, and a release controlling polymer, preferably a water-swellable release controlling polymer. As is exemplified below, a combination of HPMC and Eudragit RL, for instance in relative weight ratio's of between 1:2 and 2:1, give very good results.

In addition to the coating polymer(s), a coating may comprise one or more additives having a beneficial or otherwise desired effect on a property of the coating. Useful additives include a plasticizer, a stabiliser, a pH adjuster, a GI motility adjuster, a viscosity adjuster, a diagnostic agent, an imaging agent, an expansion agent, a surfactant, and mixtures thereof.

In one embodiment, the coating comprises a plasticizer. The group of plasticizers contains, but is not limited to, materials such as PEG6000 (also known as Macrogol 6000), triethyl citrate, diethyl citrate, diethyl phthalate, dibutyl phthalate, tributyl citrate, and triacetin. The quantity of plasticiser included will be apparent to those skilled in the art. Typically the coating may include around 2-15 wt. % plasticiser based on the total dry weight of the coating. The enteric coating may also include an anti-tack agent such as talc, silica or glyceryl monostearate.

As will be understood, floating dosage forms rely on their ability to float on gastric fluid. Gastric fluid has a density close to that of water, which is 1.004 g/ml. Therefore, for the system to remain afloat, the overall density of the system must be less than 1 g/ml. In one embodiment, a drug delivery system according to the invention has a density of less than 0.95 g/cm$^3$. Lower densities, such as less than 0.9 g/cm$^3$, more preferably less than 0.8 g/cm$^3$ are of course preferred. In a specific aspect, the density is less than 0.7 g/cm$^3$.

Of particular interest is the inclusion in the coating comprising active ingredient of an effervescent (gas forming) compound, i.e. an agent capable of generating $CO_2$ in situ upon contact with acid such as gastric fluid. This will provide the FDSS of the invention with additional buoyancy. Effervescent compounds are used already in the art of floating dosage forms and include sodium bicarbonate, sodium carbonate, or sodium glycine carbonate. However, the use of effervescent compounds has been limited primarily to either (a) single layer systems wherein gas forming material is mixed with the drug or (b) multiparticulate unit systems comprising a conventional sustained release pill, coated with a bilayer system consisting of an inner effervescent layer and an outer layer of swellable membrane (see Bardonnet et al. J Control Release 2006; 111(1-2)1-18).

The wall of the gas-filled particle is made of an aqueous soluble, erodible, disintegrating and/or biodegradable material, typically a polymer, such that the floating drug delivery system leaves no trace behind in the body. Suitable polymers that are aqueous soluble, erodible, disintegrating and/or biodegradable are well known in the art, and include gelatine and hydroxypropyl methylcellulose (HPMC).

The shape and size of the particle can vary. Of course, for oral administration purposes it is preferred that the particle can be swallowed. A preferred particle is a conventional gastric erodible/soluble capsule, such as a gelatine capsule or a HPMC capsule. Soft shells are also encompassed. The particle can be a single or a multi-particulate capsule. In one embodiment, the invention provides a FDDS comprising a capsule having a hollow, gas-filled core bordered by a wall of at least one aqueous soluble, erodible, disintegrating or degradable material, typically a polymer, said wall being surrounded by a coating comprising at least one active ingredient. In view of gastric retention time, it is preferred that an oral gastro-retentive dosage form is as large as possible (to minimize passage through the pylorus) yet sufficiently small to be swallowed. Preferably, a FDDS provided herein comprises an oblong shaped capsule having a length of at least 10 mm, preferably at least 14 mm, more preferably at least 16 mm, most preferably at least 19 mm, and/or a diameter of at least 5 mm preferably at least 6 mm, more preferred at least 7, most preferred at least 8 mm. Suitable capsules include those referred to in the art as Type 5, 4, 3, 2, 2el, 1, 1el, 0, 0el, 00, 00e1 or 000 capsules. Alternatively, wide body capsules (BDCaps®) may be used. These capsules are referred to in the art as E, D, C, B, A, AA, AAel or AAA.

The FDDS as described herein provides an alternative gastro-retentive dosage form that is simple and relatively cheap to manufacture. A floating drug delivery system (FDDS) comprising active ingredient can be prepared using a method comprising the steps of (a) providing a gas-filled particle made of at least one aqueous soluble, erodible, disintegrating or degradable polymer and (b) providing a coating solution or a coating dispersion comprising active ingredient, a coating polymer, optionally additives, in a volatile solvent. Then, at least one layer of coating dispersion is applied onto the surface of particle, typically by spraying or dip coating. Application may be direct onto the aqueous soluble, erodible, disintegrating or degradable material, typically a polymer, making up the wall of the particle. Alternatively, the wall may first be provided with a sub-coating, on which the coating comprising active ingredient is applied. Upon the evaporation of the volatile solvent, a solid coating serving as "drug release layer" is obtained. Furthermore the active ingredient-containing layer may be covered by a top-coating that improve the appearance of the capsule (e.g. giving it a colour) or contain taste-masking components. Step (a) preferably entails the manufacture of a conventional air-filled capsule according to well-established methods. The capsule can be a two-part conventional capsule as well as a single unit air filled capsule. Step (b) in itself is also standard practice in the art of controlled release dosage forms. The skilled person will be able to choose the type(s) and relative amount(s) of the components to obtain a coating solution or a coating dispersion that provides the particle with a drug coating having the desired release properties. A suitable volatile solvent is an alcohol, such as ethanol or isopropanol. Alternatively aqueous solutions or suspensions could be used. The solution or dispersion may contain between about 10 and 600 gram of dry matter per liter solvent, such as between 50 and 150 gram per liter. The concentrations and relative amount of active ingredient in the coating dispersion may depend on the dosage amount to be achieved. In general, the coating dispersion will contain between about 1 and 50 wt % of active ingredient based on the total dry weight of the dispersion. It is important that the coating dispersion is sufficiently homogeneous to obtain a good coating uniformity. This can be achieved by thorough mixing. When dip coating is applied even higher amounts of dry matter could be added to the volatile solvent. An aspect of the invention relates to the above-described methods for providing a floating drug delivery system (FDDS).

As will be illustrated in the examples here below, the FDDS of the present invention can be loaded with relatively high amounts of active ingredient, i.e. as compared to other types of floating drug delivery systems. Depending on the target subject and/or dosage regimen, suitable dosage forms of the FDDS can be developed. In one embodiment, the FDDS comprises a particle (capsule) having a hollow, gas-filled core bordered by a wall of at least one aqueous soluble, erodible, disintegrating or degradable polymer, said wall being surrounded by a coating comprising 10 mg to 10 gram of active ingredient. Preferably, the coating comprises 20 to 8000 mg of active ingredient, more preferably 25 to 5000, such as 20-1000, 50-500 or 1000-2500. Preferred examples of the FDDS of the invention contain active ingredient in a total amount of 100, 150 mg, 200 mg, 250 mg, 300 mg, 400 mg, 500 mg or 600 mg.

A floating drug delivery system as provided herein is advantageously used for the treatment or prophylaxis of a disease, for example in a method comprising administering to a patient in need thereof a composition comprising a floating drug delivery system (FDDS) according to the invention, wherein the at least one active ingredient is capable of treating or preventing the disease. The FDDS is preferably formulated for oral administration. In one embodiment, a method of the invention comprises administering to a patient in need of such treatment or prophylaxis a composition comprising an oral floating drug delivery system (FDDS), the system comprising a controlled release coating comprising at least one active ingredient against the disease coated onto the surface of a solid particle, said particle having a hollow, gas-filled core bordered by a wall of at least one aqueous soluble, erodible, disintegrating or degradable material, typically a polymer. It will be understood that an FDDS of the invention, as with other floating systems, works optimal if the stomach of the subject receiving the FDDS is at least partially filled with gastric fluid. Therefore, it is preferred that the subject is a non-fasted subject. In case the subject is a fasted subjects, the method comprises administering to the subject an oral floating drug delivery system (FDDS) together with a sufficient amount of fluid, e.g. an amount of water of at least 100 ml, preferably at least 200 ml.

In one aspect, the invention provides a method for treating or preventing a disease which is located in the stomach or upper intestinal tract, comprising administering to a patient in need thereof a composition comprising a floating drug delivery system (FDDS) according to the invention, and wherein the active ingredient is useful in the local treatment of the disease. In another aspect, the invention provides a method for treating or preventing a disease, comprising oral systemic drug administration, and wherein the active ingredient is absorbed into the systemic circulation from only a limited part of the intestinal tract.

A FDDS of the invention is particularly useful for delivering a therapeutic agent to the stomach or upper intestinal tract of a patient and/or for enhancing the gastric retention of an agent in the stomach of a patient, the method comprising oral administration to the patient of a composition comprising a floating drug delivery system (FDDS), wherein a coating comprising the therapeutic agent is coated onto the surface of a solid particle, preferably a capsule, said particle having a hollow, gas-filled core bordered by a wall of at least one aqueous soluble, erodible, disintegrating or degradable material, typically a polymer.

Also encompassed is a method of enhancing the gastrointestinal absorption of a drug which is absorbed into the systemic circulation over only a limited part of the small intestine of a patient, the method comprising oral administration to the patient of the drug being incorporated in a FDSS as provided herein.

As will be understood by those skilled in the art, the principal features of this invention can be employed in the various aspects and embodiments without departing from the scope of the invention. More, in particular, it is contemplated that any feature discussed in this specification can be implemented with respect to any of the methods, compositions and uses of the invention, and vice versa.

Furthermore, for a proper understanding of this invention and its various embodiments it should be understood that in this document and the appending claims, the verb "to comprise" is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The following examples describe various new and useful embodiments of the present invention. It will be understood that particular embodiments described herein are shown by way of illustration and not as limitations of the invention. Those skilled in the art will recognize, or be able to ascertain using no more than routine experimentation, numerous equivalents to the specific procedures described herein. Such equivalents are considered to be within the scope of this invention and are covered by the claims.

Example 1

A typical example of a gastro-retentive system can be obtained by coating of an empty gelatine capsule with coating comprising at least one pharmacologically active ingredient.

In a specific embodiment the gelatine capsule is coated with a suspension containing:

drug (e.g. nicotinamide): 1 to 95% of the solids in the suspension;

polymers and release controlling agents: 5 to 99% of the solids in the suspension.

The amount of drug that will be sprayed onto the capsule is determined by the desired dose of the drug and the concentration of the drug in the coating. The composition of the drug containing coating layer is determined by the desired release profile. Typical polymers like Hypromellosum 4000 mPa·s., viscosity2% m/V or Eudragit RL PO can be used whereas plasticizers such as Polyethylenglycolum 6000 or dibutyl phthalate can be used. Other excipients that can be used in the coating suspension are magnesium stearate, talc or mannitol. The coating suspension is applied on the gelatine capsules in equipment such as fluidized beds or perforated pan-coaters.

A second example of a gastro-retentive system can be obtained by the incorporation of gas-forming materials in a tablet that contains a hydrophilic gel forming polymer.

In a specific embodiment such a tablet would contain:

| drug | 0.5 to 90%; |
|---|---|
| HPMC 4000 | 10 to 80%; |
| sodium carbonate | 5 to 20%; |
| Sodium stearyl fumarate | 0.5 to 5%. |

Furthermore excipients such as fillers, binders, glidants, lubricants and others known in the art of tablet formulation can be added to the formulation. The tablets can be made according to well known tablet production technologies such as direct compaction, dry granulation or wet granulation techniques. Tablet compaction can be performed using tablet machines widely known in the pharmaceutical industry.

Example 2: Dissolution of Nicotinamide from FDDS

Materials

HPMC (Hypromellosum 4000 mPa·s., viscosity2% m/V) was obtained from Bufa BV, Uitgeest, The Netherlands. Macrogol 6000 (Polyethylenglycolum 6000) was obtained from Fagron, The Netherlands. Eudragit RL PO (Pharma Polymere, Rohm GmbH) was obtained from Chemische Fabric, Kirschenallee, Darmstadt, Germany. Nicotinamide Ph.Eur.quality was used.

Methods

A number of different coating dispersions (also referred herein as "suspensions") were prepared (see Table 1). The required amount of HPMC was weighted to a beaker and then mixed with Ethanol (100 ml). Subsequently, the nicotinamide was added in the amounts indicated below. In parallel, in another beaker Macrogol 6000 was prepared by melting at a temperature not higher than 80° C., after melting, ethanol (50 ml) was added and subsequently the required amount of Eudragit RL PO was added. The cooled solution was mixed with the contents of the first beaker to provide a coating dispersion.

TABLE 1

| composition of the different coating suspensions. | | | |
| --- | --- | --- | --- |
| Ingredient | Coating 1 | Coating 2 | Coating 3 |
| HPMC | 4.0 g | 4.0 g | 5.0 g |
| Eudragit RL PO | 3.5 g | 3.5 g | 3.5 g |
| Macrogol 6000 | 1.0 g | 1.0 g | 1.0 g |
| nicotinamide | 5.0 | 1.0 | 5.0 |
| ethanol | 150 ml | 150 ml | 150 ml |

Hard gelatine capsules (No. 3) were coated with the different coating dispersions using an appropriate spray nozzle according to standard procedures. Briefly, the coating dispersion was sprayed onto the surface of the capsules rotating in a small container under a heated air stream until the required amount of drug-polymer mixture as determined by weight analysis was sprayed on the capsules.

Dissolution test were performed in a beaker with 500 ml of 0.1 M HCl at pH=1.03-1.09 at a temperature of 34-38° C. while stirring at 150 rpm using a magnetic stirrer.

Samples (2.5 ml) were taken every 30 minutes up to 7 hours with a syringe. The samples were analysed at 280 nm for the content of active ingredients using a spectrophotometer.

Results

Four capsules were coated with coating dispersion 1, and two of them were subjected to the dissolution test in a beaker with 500 ml of 0.1N HCl. After six hours, more than 95% of active substance was released, showing that drug release was complete after 6 hours. The capsule was still floating on the 0.1N HCl after 24 hours.

Coating dispersion 2 was used to coat four capsules, and two of them were subjected to the dissolution test. After six hours, more than 90% of active substance was released. The capsule was still floating on the 0.1N HCl after 24 hours.

Coating dispersion 3 was used to coat another four capsules and two of them were subjected to the dissolution test. After six hours, less than 50% of active substance was released. The higher quantity of HPMC in coating 3 leads to a slower release of active substance. Moreover the release was incomplete. This shows that, by varying the polymer content of the coating composition, the rate of drug release from the floating particle can be altered. The capsule was still floating on the 0.1N HCl after 24 hours.

Example 3: Development of a 300 mg and a 600 mg Nicotinamide Gradient FDDS

Background

The concept of an FDDS comprising several layers of distinct composition and distinct amounts of nicotinamide was tested. Also the concept of an FDDs comprising an outer coating layer comprising no nicotinamide was tested.

The aim of the experiment was to optimize the formulation, especially to prevent an initial release burst and to prolong the period of constant nicotinamide release, preferably over the entire residence time of the FDDS in the stomach. This involved testing of formulations containing outer coatings containing a high percentage of hypromellose and outer coatings containing no nicotinamide as well as formulations containing an inner layer with a high percentage of starch.

Materials & Methods

Nicotinamide was purchased from Sigma-Aldrich, hypromellose 400 mPa·s from Bufa, Starch 1500 from Colorcon and magnesium stearate from Genfarma by. In all experiments demineralized water was used. The release profiles were determined in 0.01N HCl. For the preparation of coating suspensions acetone was used.

Hypromellose is a swelling agent that is used to delay the release of nicotinamide. The hydrophilic drug is released via diffusion. Starch and magnesium stearate show a faster release of nicotinamide. This influence of the various excipients has been investigated.

To prepare the floating delivery system, a suspension containing the excipients and the drug were sprayed on empty hollow capsules. This was done using a spray-coat system. The different substances are dissolved in water and acetone. The suspension should be slightly viscous to prevent sedimentation and blockage in the system. The ratio of acetone and distilled water depends on the amount of hypromellose. At a low concentration of hypromellose relatively more water is used so that the suspension has the desired viscosity. The substances are first suspended and/or dissolved in acetone prior to adding water. This prevents formation of lumps in the slurry. The suspension is sprayed through a nozzle (1 mm) together with air, so that small droplets are introduced into the spraying sphere. The spraying sphere is heated from the outside so that the acetone evaporates quickly and the substances are coated on the capsules. Capsule sizes 3, 4 and 5 (Spruyt Hillen) were used in various experiments. It was decided that capsule size 4 was used which were 'locked' by pressing the halfs together so as to somewhat reduce the size.

The coatings consisted of different formulations with different concentrations of nicotinamide, hypromellose, magnesium stearate and starch, as will be described here below.

The produced capsules were tested for their floating behaviour and release profile in a dissolution bath (Prolabo) filled with 1 liter 0.01 N HCl, 37±1° C., at 50 rpm. The 0.01 N HCl was prepared by degassing 6 liter of demineralized water and adding 8 ml 25% HCl. The release profiled were determined for at least 12 hours by UV absorbance measurements at 280 nm (cuvet 1 cm) (Ultrospec III, Pharmacia LKB). The floating behaviour was followed by visual inspection. All experiments were performed in 2-, 3- or 5-fold.

The final formulation for a 300 mg gradient FDDS comprises 3 layers. The first layer surrounding the capsule has a concentration of 80% nicotinamide (200 mg active). The second layer 50% (100 mg active), and the third layer 0% (90 mg coating material). The composition is shown in Table 2.

TABLE 2

| composition of 300 mg nicotinamide FDDS. | | | |
| --- | --- | --- | --- |
| Component | 80% | 50% | 0% |
| Nicotinamide | 79% | 49% | — |
| Hypromellose | 16% | 40% | 78% |
| Starch 1500 | 4% | 10% | 20% |
| Magnesium stearate | 1% | 1% | 2% |
| Amount of active | 200 mg | 100 mg | — |

The final formulation for the 600 mg gradient FDDS comprises 2 layers. The inner layer consists of 80% nicotinamide. The layer comprises 750 mg of the coating material.

Around it is a 0% coating of 150 mg. A SEM image was made of a crosssection of the FDDS in which both layers could clearly be distinguished. The composition of this FDDS is shown in Table 3.

TABLE 3 composition of 600 mg nictoinamide FDDS.

| Component | 80% | 0% |
|---|---|---|
| Nicotinamide | 79% | — |
| Hypromellose | 16% | 78% |
| Starch 1500 | 4% | 20% |
| Magnesium stearate | 1% | 2% |
| Amount of active | 600 mg | — |

Results

Figure 2:
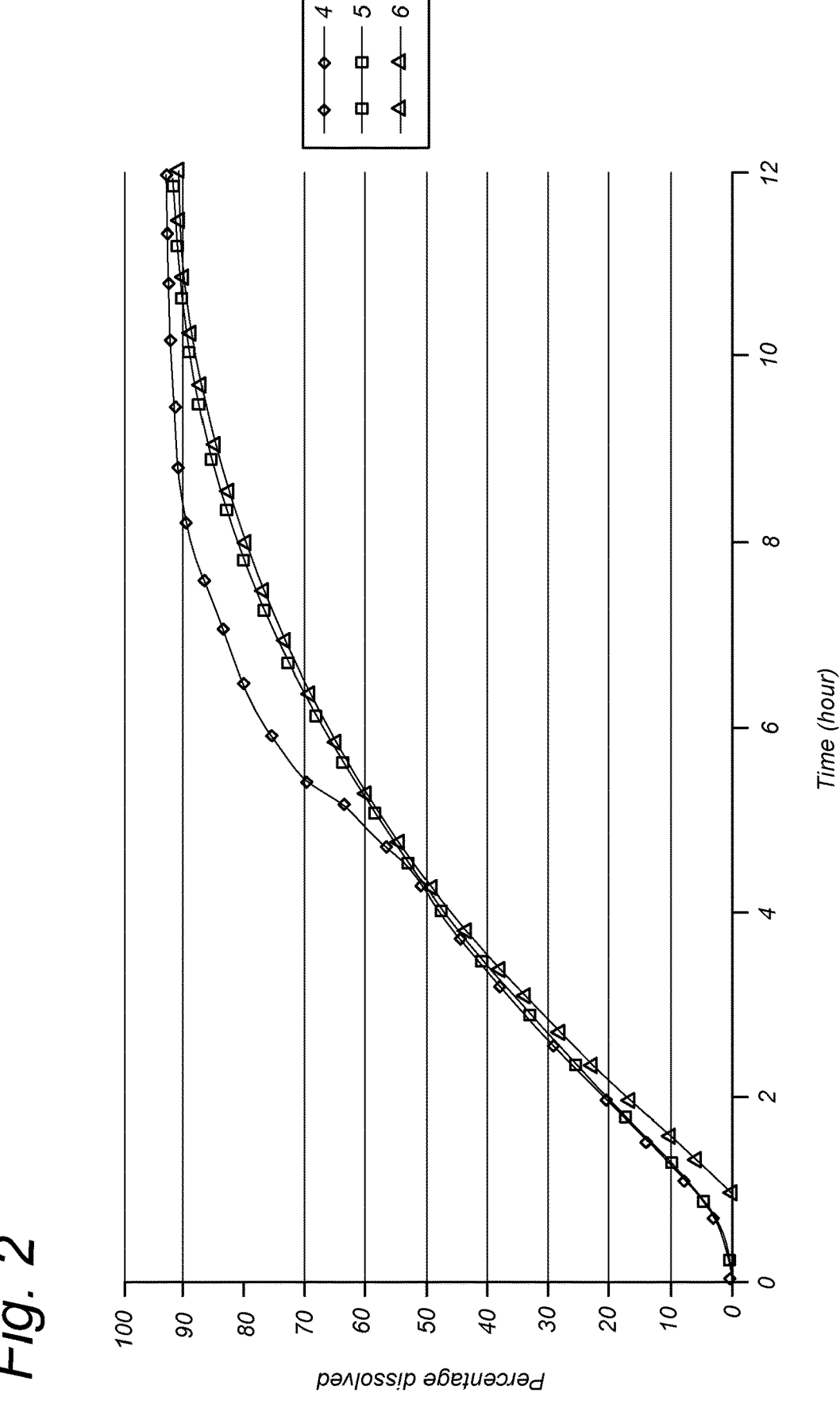
FIG. 2 illustrates a release profile of the 600 mg FDDS.

FIGS. 1 and 2 show the release profiles of the 300 mg FDDS and 600 mg FDDS respectively. A satisfactory release rate is accomplished nearly over the entire 12 hour period. The results show that the release profiles of the 300 en 600 mg FDDS's are comparable.

The floating behaviour of both the FDDS's was also tested in milk, simulating an environment containing substantial amounts of fat. The FDD S's staid afloat for more than 12 hours.

Discussion/Conclusion

The 300 and 600 mg nicotinamide gradient FDDS's are capable of staying afloat for at least 12 hours and of releasing nicotinamide at a substantially constant rate for almost the entire 12 hour period.

To achieve this near constant release the FDDS's were designed to comprise different layers of coating. For example, the 300 mg FDDS contained an inner layer with 200 mg nicotinamide (80% based on the total weight of the layer), a middle layer with 100 mg nicotinamide (50% based on the total weight of the layer) and an outer layer that did not contain nicotinamide. The 600 mg FDDS contained an inner layer with 600 mg nicotinamide (80% based on the total weight of the layer) and an outer layer that did not contain nicotinamide.

The use of distinct layers allowed for the regulation of the overall release profile, to achieve near constant release rates of periods of up to 12 hours.

Example 4: Effects of Rupture of FDDS on Floating Capability and Release Profile Background The present inventors decided to also investigate the effects of mechanical damage to the FDDS. It was envisaged that damaging of the formulation could easily arise when treating young children as they might, for instance, 'accidentally' chew or crush the FDDS before swallowing. The floating behaviour and release profiles of ruptured capsules were therefore tested and compared to the floating behaviour and release profiles of intact FDDS's.

Materials & Methods

The FDDS's used for this experiment were of the multilayer gradient type. They were prepared and tested using the protocols described in example 3. The composition is shown in table 4.

TABLE 4 composition of FDDS for rupturing experiment

| | 80% | 50% | 0% |
|---|---|---|---|
| Hypromellose | 16% | 19% | 78% |
| Starch 1500 | 4% | 10% | 20% |
| Magnesium stearate | 1% | 1% | 2% |
| Nicotinamide | 79% | 50% | — |

Each FDDS contained 45 mg 0% coating.

Each FDDS contained 45 mg 0% coating.

The FDDS's proved to be strong and difficult to damage. The FDDS's were placed in a bench vice that was tightened until the wall of the FDDS began to rupture. The crushing strength was over 200 N for all products.

The floating behaviour as well as the release profile was determined of both the damaged and undamaged the FDDS's.

Results

All FDDS's, ruptured and undamaged, staid afloat in the testing liquid. After 18 hours remains were still afloat in the dissolution beakers.

Figure 3:
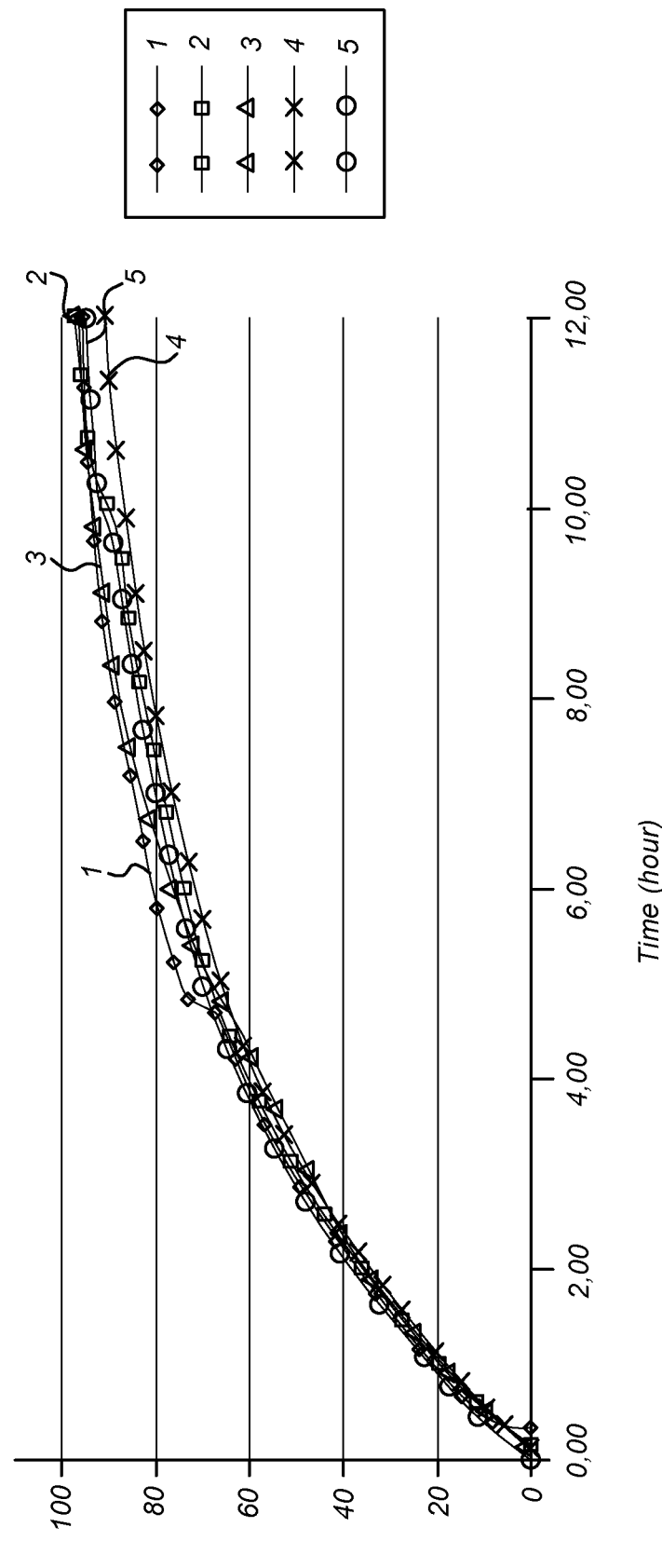
FIG. 3 illustrates release profiles of the FDDS's.

The release profiles of the FDDS's are shown in FIG. 3. As can be seen in said figure, the release profiles of capsule 1 and 2 (undamaged FDDS's) did not differ significantly from that of capsules 3 and 4 (ruptured FDDS's). During the first 4 hours, the release profiles are identical. After 4 hours a minor difference becomes apparent in that the release rate of the ruptured FDDS is slightly higher than that of the non-damaged FDDS's. This difference is however is never more than 8%.

Conclusion/Discussion

The FDDS of the invention is capable of staying afloat even after mechanical damage and rupture. The damage hardly affects the nicotinamide release profile. Possibly, because of the swelling of the hypromellose upon contact with water, cracks in the wall are effectively closed restoring the integrity of the FDDS.

Example 5: In Vivo Release of Nicotinamide in Healthy Human Volunteers Using FDDS Healthy adults, 4 women and 4 men, were recruited as volunteers in a trial to investigate the pharmacokinetic profile of the nicotinamide FDDS of the invention. The trial was performed with 300 and 600 mg FDDS formulations as described in example 3.

During the trial blood was sampled at pre-determined intervals. Samples (Li— heparin) were collected and frozen for storage. In addition urine was collected (24h). The entire protocol was as described in table 5.

TABLE 5

Protocol for determining PK profile of Nicotinamide FDDS

Start of trial
7:30   Arrival of subjects (empty stomach) at test location. Canule for blood sampling is placed.
       Blood sample T0
8:00   Subjects have breakfast (1-2 sandwiches) and drinks (tea, fruit juice)
8:15   Subjects ingest nicotinamide FDDS
8:45   Blood sample T1
9:45   Blood sample T2
10:45  Blood sample T3
       Subjects have drinks (tea, coffee, water and/or juice)

TABLE 5-continued

| Protocol for determining PK profile of Nicotinamide FDDS | |
|---|---|
| 11:45 | Blood sample T4 |
| 12:30 | Subjects have lunch (3-4 sandwiches) and drinks ((tea, coffee, water, and/or juice) |
| 13:00 | Blood sample T5 |
| 16:00 | Blood sample T6 |
| | Subjects have drinks (tea, coffee, water and/or juice) |
| After 16:00 | Subjects go home. Subjects continue to collect their urine samples. At home the subjects have dinner and drinks (standard) and are told not to take alcohol containing drinks |
| 7:30 (next day) | Arrival of subjects (empty stomach) at test location and hand over their urine samples. |
| 8:00 | Blood sample T7 |
| End of trial | |

Figure 4:
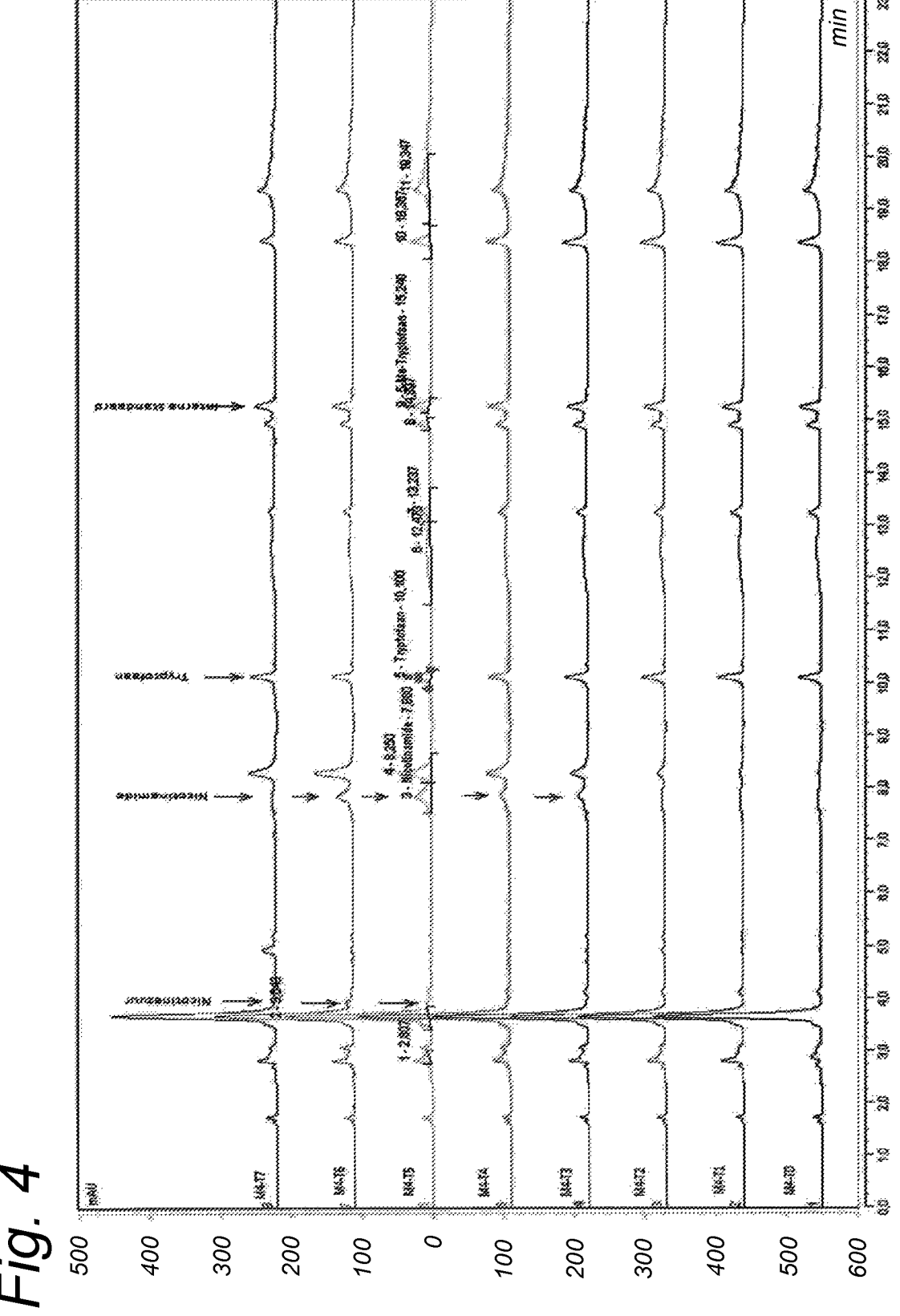
FIG. 4 illustrates detection of nicotinamide in plasma.

The stored Li-heparin samples were analyzed using a standard HPLC measurement. Measurements were performed with and without protein removal from the plasma, as it appeared that the protein removal negatively affected resolution of the analyte(s). These problems, which could not be resolved instantaneously, did however not prohibit the detection of the nicotinamide in the various samples. For illustrative purposes, FIG. 4 is referred to, showing the detection of nicotinamide in the plasma of one of the test subjects. From this figure it can be inferred that the ingestion of the FDDS caused a significant and persistent increase in the subject's nicotinamide plasma level.

The overall results showed that the FDDS of the invention was capable of maintaining an increased nicotinamide plasma levels in vivo for a period of at least 8 hours after ingestion.

Example 6: Preparation of Floating Drug Delivery System with Levodopa and/or Carbidopa

Materials

Levodopa (Ph.Eur.quality), Carbidopa (Ph.Eur.5.8 quality) and HPMC (Hypromellosum 4000 mPa·s., viscosity2% m/V) were obtained from Bufa BV, Uitgeest, The Netherlands). Macrogol 6000 (Polyethylenglycolum 6000) was obtained from Fagron, The Netherlands. Eudragit RL PO (Pharma Polymere, Rohm GmbH) was obtained from Chemische Fabric, Kirschenallee, Darmstadt, Germany.

Methods

A number of different coating dispersions (also referred herein as "suspensions") were prepared (see Table 6). The required amount of HPMC was weighted to a beaker and then mixed with Ethanol (100 ml). Subsequently, the active substances were added in the amounts indicated below. In parallel, in another beaker Macrogol 6000 was prepared by melting at a temperature not higher than 80° C., after melting, ethanol (50 ml) was added and subsequently the required amount of Eudragit RL PO was added. The cooled solution was mixed with the contents of the first beaker to provide a coating dispersion.

TABLE 6

| composition of the different coating suspensions. | | | | | |
|---|---|---|---|---|---|
| Ingredient | Coating 1 | Coating 2 | Coating 3 | Coating 4 | Coating 5 |
| HPMC | 4.0 g | 4.0 g | 5.0 g | 5.0 g | 4.0 g |
| Eudragit RL PO | 3.5 g | 3.5 g | 3.5 g | 3.5 g | 3.5 g |

TABLE 6-continued

| composition of the different coating suspensions. | | | | | |
|---|---|---|---|---|---|
| Ingredient | Coating 1 | Coating 2 | Coating 3 | Coating 4 | Coating 5 |
| Macrogol 6000 | 1.0 g | 1.0 g | 1.0 g | 15 g | 1.0 g |
| levodopa | 6.0 g | — | — | 7.0 g | 7.0 g |
| carbidopa | — | 0.6 g | 0.6 g | 0.7 g | 0.7 g |
| Ethanol | 150 ml | 150 ml | 150 ml | 150 ml | 150 ml |

Hard gelatin capsules (No. 3) were coated with the different coating dispersions using an appropriate spray nozzle according to standard procedures. Briefly, the coating dispersion was sprayed onto the surface of the capsules rotating in a small container under a heated air stream until the required amount of drug-polymer mixture as determined by weight analysis was sprayed on the capsules.

Dissolution test were performed in a beaker with 500 ml of 0.1 M HCl at pH=1.03-1.09 at a temperature of 34-38° C. while stirring at 150 rpm using a magnetic stirrer.

Samples (2.5 ml) were taken every 30 minutes up to 7 hours with a syringe. The samples were analysed at 280 nm for the content of active ingredients using a spectrophotometer. When the combination capsules were analysed the absorption was assumed to be caused by both the levodopa and the carbidopa in the same ratio as they were present in the product. The assumption that both the drug release and the contribution to the absorption were relative to the presence of both components in the product can be justified by the fact that the solubility of both materials is within the same order of magnitude and by the fact that the specific absorption of the materials differs less than 20%.

Results

All gelatin capsules were floating on the stirred 500 ml of 0.1N HCl up to a period of at least 24 hours from the onset of the experiment.

Four capsules were coated with coating suspension 1, and two of them were subjected to the dissolution test in a beaker with 500 ml of 0.1N HCl. The discussed capsule contained 87.4 mg levodopa which was present in the polymer coating in a concentration of 41.4%. After six hours, 87.38 mg of active substance was released, showing that drug release was complete after 6 hours. The capsule was still floating on the 0.1N HCl after 24 hours.

Figure 5:
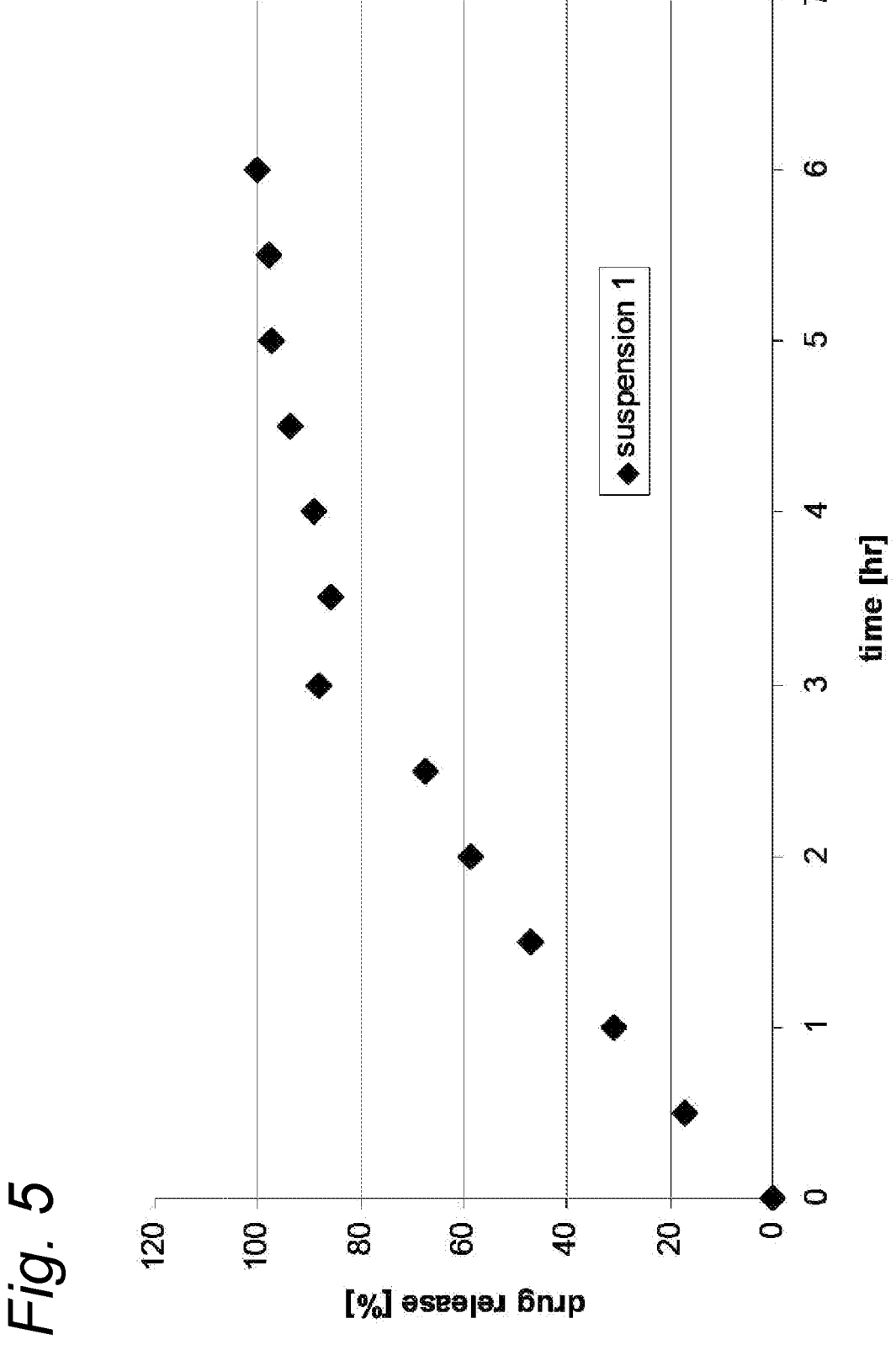
FIG. 5 illustrates dissolution profiles of a capsule coated with levodopa.

FIG. 5 illustrates the dissolution profiles of a capsule coated with levodopa in a coating comprising HPMC. Drug release is expressed as percentage of the theoretical maximum. The figure shows a representative levodopa release profile obtained with coating suspension 1. The levodopa concentration in the simulated gastric fluid gradually increases up to 5 hours, after which it remained almost constant.

Figure 6:
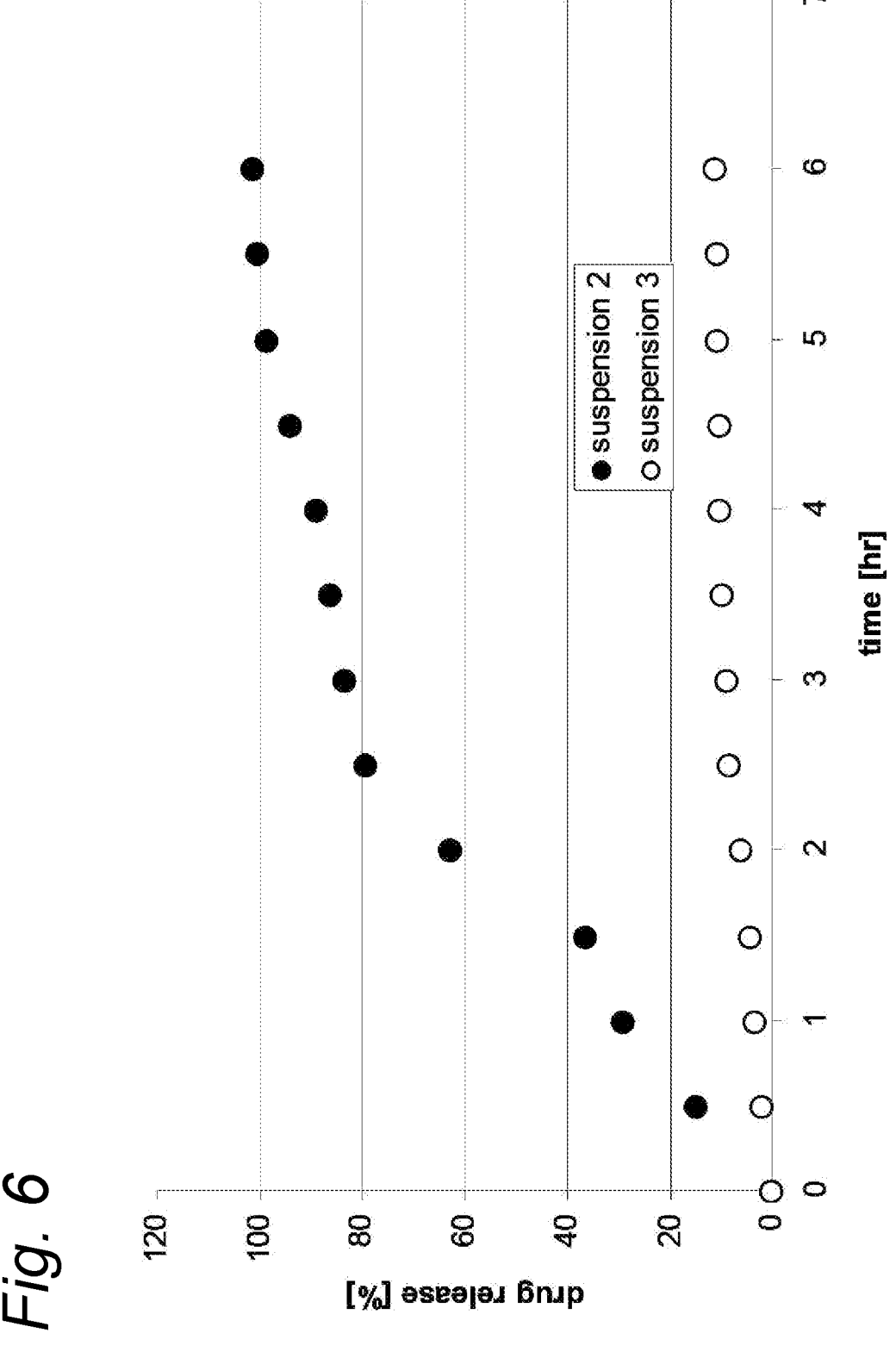
FIG. 6 illustrates dissolution profiles of a capsule coated with carbidopa.

Coating suspension 2 was used to coat four capsules with carbidopa, and two of them were subjected to the dissolution test. The discussed capsule contained 11.67 mg carbidopa, constituting 6.59 wt % of the coating composition based on dry weight. After six hours, 10.125 mg of active substance was released. FIG. 6 illustrates the dissolution profiles of a capsule coated with carbidopa in a coating comprising different amounts of HPMC (see Table 6). Drug release is expressed as percentage of the theoretical maximum. FIG. 6 shows a representative carbidopa release profile obtained with coating 2.

Coating suspension 3 was used to coat another four capsules and two of them were subjected to the dissolution test. The discussed capsule contained 10.50 mg carbidopa, constituting 5.94 wt % of the coating composition based on dry weight. After six hours, 1.14 mg of active substance was released. FIG. 6 shows a representative carbidopa release profile obtained with coating 3. The higher quantity of HPMC in coating 3 leads to a slower release of active substance. Moreover the release was incomplete. This shows that, by varying the polymer content of the coating composition, the rate of drug release from the floating particle can be altered.

Next, coating suspensions 4 and 5 comprising a mixture of levodopa and carbidopa as active ingredients were evaluated.

Figure 7:
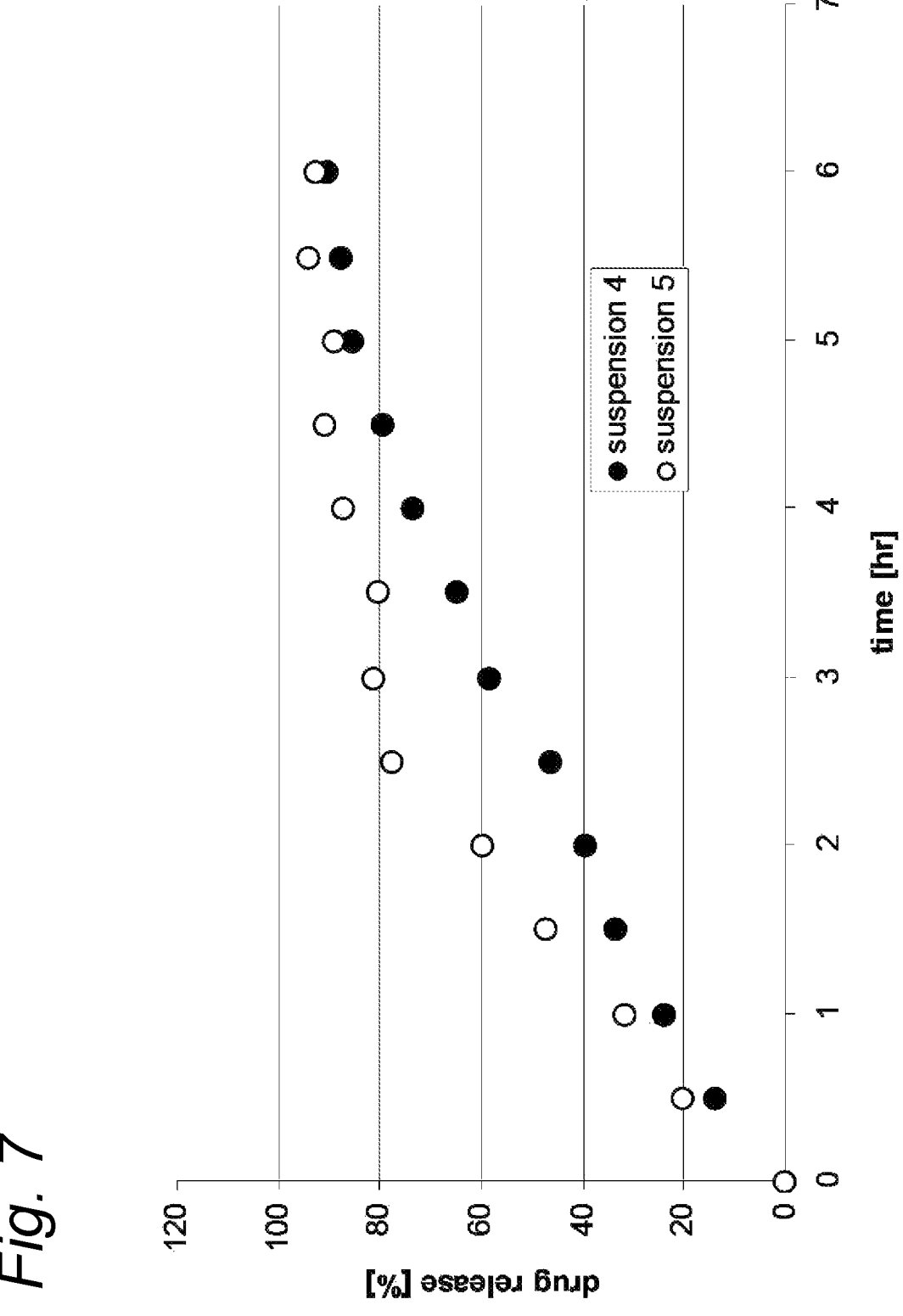
FIG. 7 illustrates dissolution profiles of a capsule coated with the combination of levodopa and carbidopa.

FIG. 7 illustrates the dissolution profiles of a capsule coated with the combination of levodopa and carbidopa in a coating comprising different amounts of HPMC (see Table 6). Drug release is expressed as percentage of the theoretical maximum. The figure shows that the release of levodopa and carbidopa from a capsule coated with suspension 4 increases steadily in time. A capsule contained 97.13 mg levodopa and 9.71 mg carbidopa which were present in the coating at concentrations of 39.55% and 3.95% respectively. In contrast, absorption of carbidopa and levodopa combination in a market available normal dosage form like tablets is rapid and virtually complete in 2-3 h. Extended-release tablets absorption is gradual and continuous for 4-8 h, although the majority of the dose is absorbed in 2 to 3 h. FIG. 7 also shows the drug release from a capsule coated with suspension 5. The reduced amount of HPMC in the coating resulted in a somewhat faster release of the drug.

Example 7: Development of a (+/−) 300 mg Levodopa FDDS

Four different floating drug delivery systems are produced in accordance with this invention, containing Levodopa as the active ingredient:

Levodopa 1: size 4 capsule coated with a first layer containing 79% levodopa (dry solids weight percentage) and a combination of hypromellose, in a high hypromellose to starch ratio and a second layer of said hypromellose starch combination with 0% levodopa;

Levodopa 2: size 4 capsule coated only with a layer containing 79% levodopa (dry solids weight percentage) and a combination of hypromellose, in a high hypromellose to starch ratio;

Levopdopa 3: size 4 capsule coated with a first layer containing 79% levodopa (dry solids weight percentage) and a combination of hypromellose, in a low hypromellose to starch ratio and a second layer of said hypromellose starch combination with 0% levodopa; and Levodopa 4: size 4 capsule coated only with a layer containing 79% levodopa (dry solids weight percentage) and a combination of hypromellose, in a low hypromellose to starch ratio.

The precise compositions of the FDDSs and the suspensions used for producing them is given in the following tables.

| | Levodopa 1 | | | |
| --- | --- | --- | --- | --- |
| | 79% Ldopa coating | | 0% Ldopa coating | |
| | FDDS | suspension | FDDS | suspension |
| Levodopa | 79% | 8 g | — | — |
| Hypromellose | 16% | 1.6 g | 79% | 3.2 g |

-continued

| | Levodopa 1 | | | |
| --- | --- | --- | --- | --- |
| | 79% Ldopa coating | | 0% Ldopa coating | |
| | FDDS | suspension | FDDS | suspension |
| Pregelatinized starch | 4% | 0.4 g | 20% | 0.8 g |
| Magnesium stearate | 1% | 0.1 g | 1% | 0.1 g |
| Aceton | — | 90 ml | — | 60 ml |
| Water | — | 15 ml | — | 7 ml |
| Capsule size | Size 4 'pressed to lock' | | | |
| Amount on FDDS | corr. to 330 mg of Ldopa | | 67 mg of coating | |

| | Levodopa 2 | | | |
| --- | --- | --- | --- | --- |
| | 79% Ldopa coating | | 0% Ldopa coating | |
| | FDDS | suspension | FDDS | suspension |
| Levodopa | 79% | 8 g | — | — |
| Hypromellose | 16% | 1.6 g | — | — |
| Pregelatinized starch | 4% | 0.4 g | — | — |
| Magnesium stearate | 1% | 0.1 g | — | — |
| Aceton | — | 90 ml | — | — |
| Water | — | 15 ml | — | — |
| Capsule size | Size 4 'pressed to lock' | | | |
| Amount on FDDS | corr. to 330 mg of Ldopa | | 0 mg of coating | |

| | Levodopa 3 | | | |
| --- | --- | --- | --- | --- |
| | 79% Ldopa coating | | 0% Ldopa coating | |
| | FDDS | suspension | FDDS | suspension |
| Levodopa | 79% | 8 g | — | — |
| Hypromellose | 4% | 0.4 g | — | — |
| Pregelatinized starch | 16% | 1.6 g | — | — |
| Magnesium stearate | 1% | 0.1 g | — | — |
| Aceton | — | 90 ml | — | — |
| Water | — | 15 ml | — | — |
| Capsule size | Size 4 'pressed to lock' | | | |
| Amount on FDDS | corr. to 330 mg of Ldopa | | 0 mg of coating | |

| | Levodopa 4 | | | |
| --- | --- | --- | --- | --- |
| | 79% Ldopa coating | | 0% Ldopa coating | |
| | FDDS | suspension | FDDS | suspension |
| Levodopa | 79% | 8 g | — | — |
| Hypromellose | 4% | 0.4 g | 78% | 0.8 g |
| Pregelatinized starch | 16% | 1.6 g | 20% | 0.2 g |
| Magnesium stearate | 1% | 0.1 g | 2% | 0.025 g |
| Aceton | — | 90 ml | — | 25 ml |
| Water | — | 15 ml | — | 2 ml |
| Capsule size | Size 4 'pressed to lock' | | | |
| Amount on FDDS | corr. to 300 mg of Ldopa | | 15 mg of coating | |

Floating Capacity and Release Profiles

Release profiles of Levodopa from all FDSSs was tested using the USP dissolution system II (paddle method) (Prolabo) with 1 L of 0.01 N HCl as the dissolution medium (T=37±1° C.). All FDDSs remained afloat in the dissolution bath during the entire period of testing (12 hours).

Figure 8:
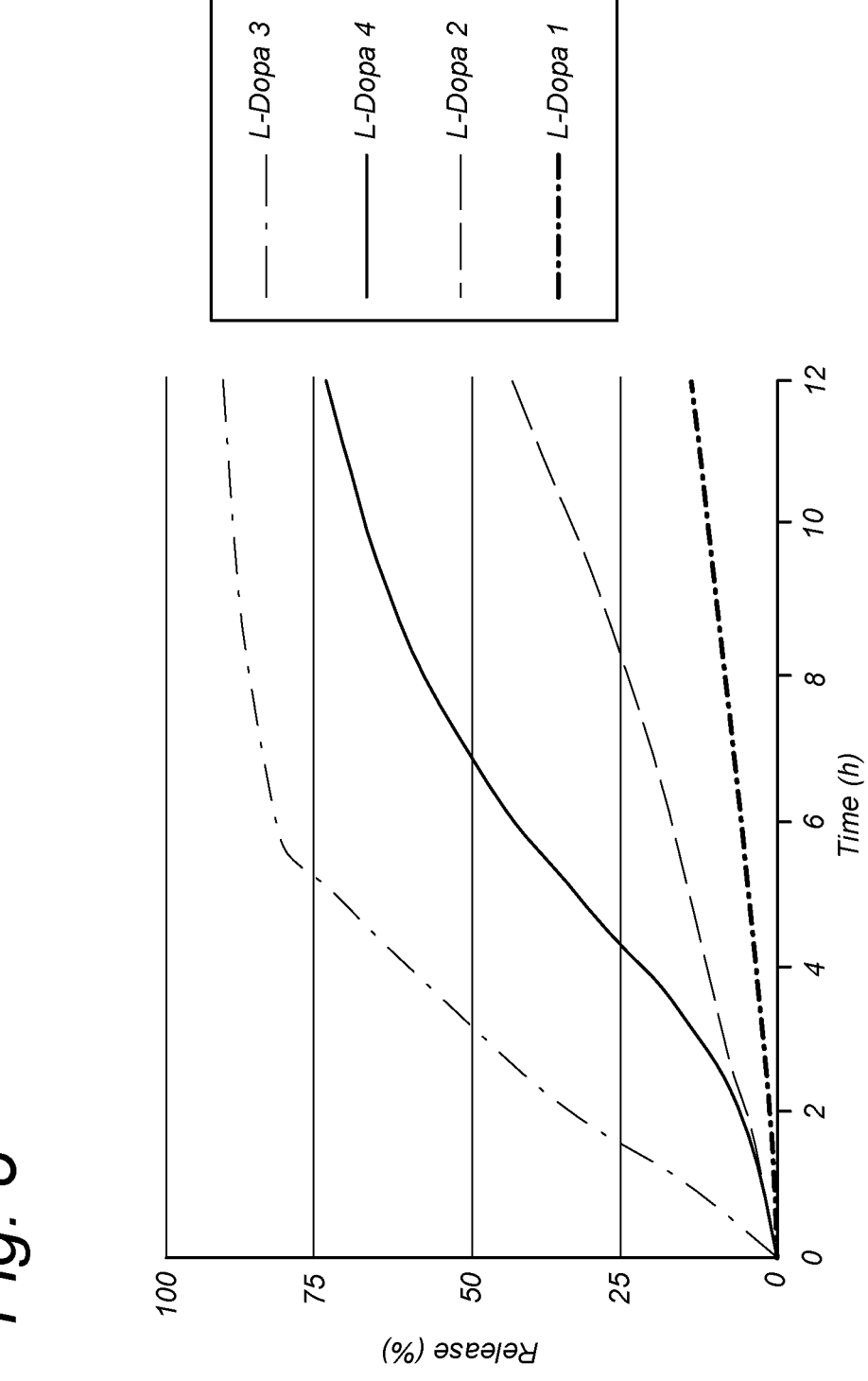
FIG. 8 illustrates the release curves of the levodopa 1-4.
Figure 9A:
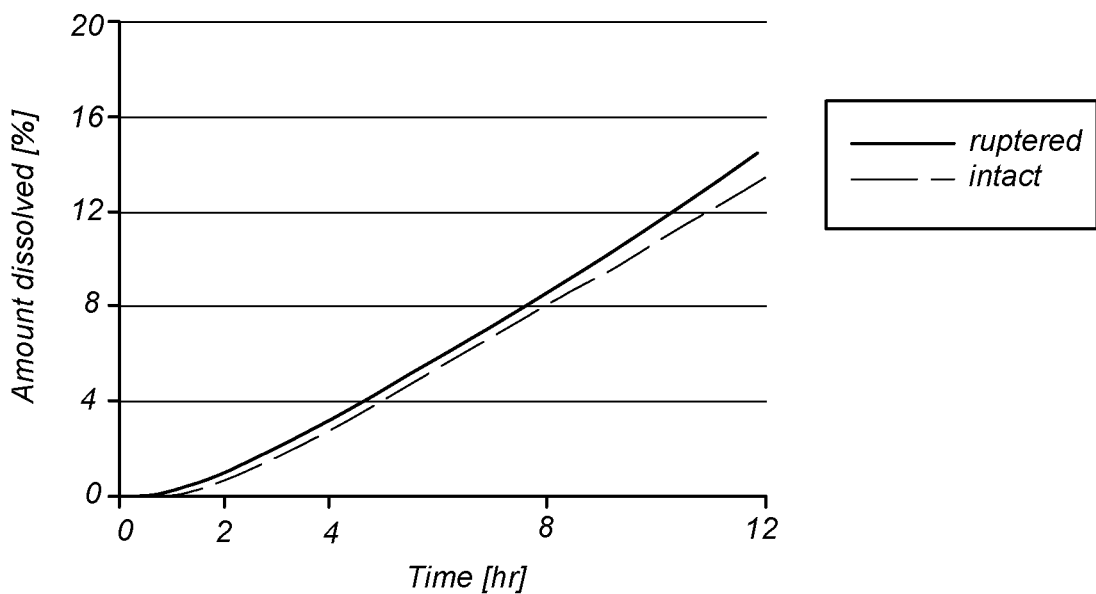
FIGS. 9a-9d illustrate release profiles of the damaged and undamaged FDDSs.
Figure 9B:
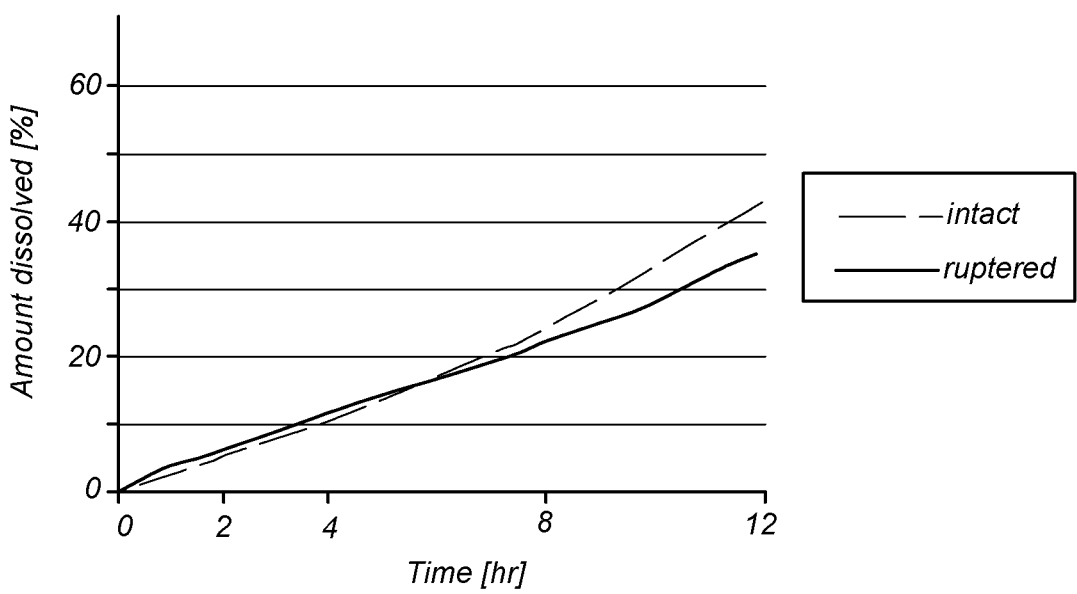
Figure 9C:
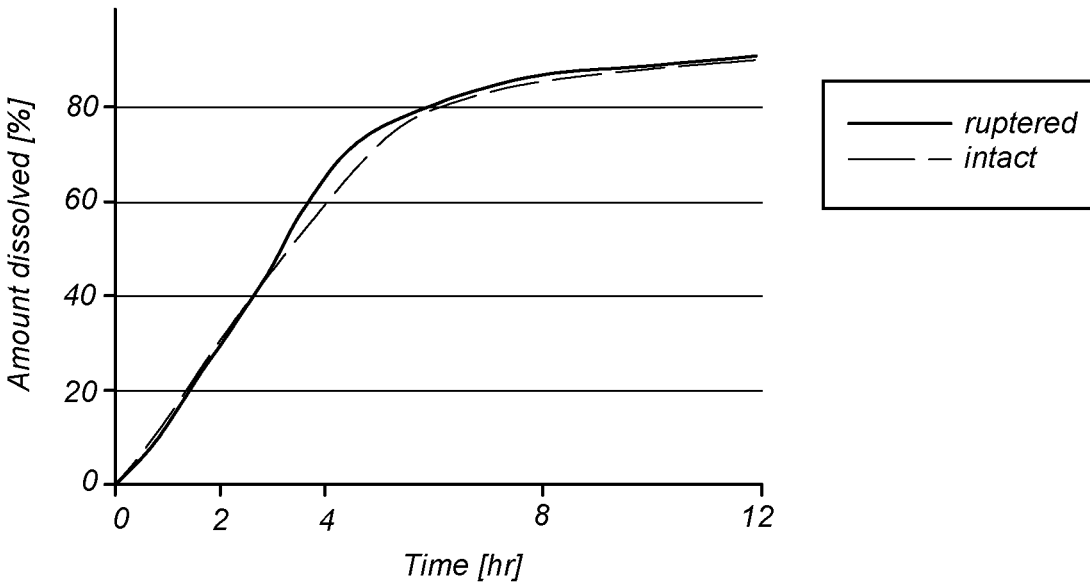
Figure 9D:
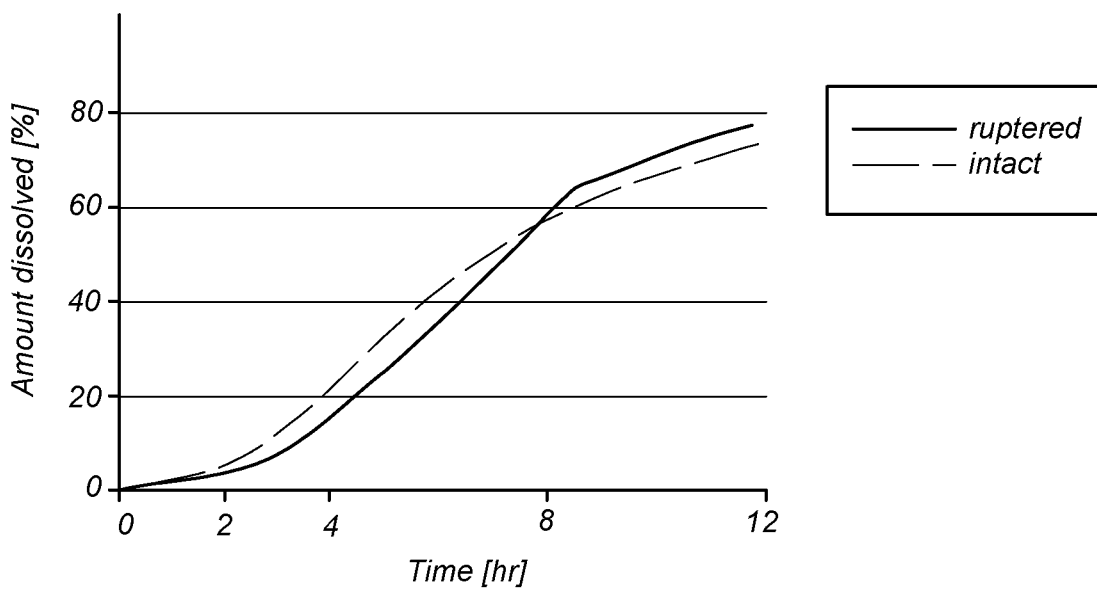

In FIG. 8 the release curves of the levodopa 1-4 have been plotted (percentage of the total Ldopa content dissolved vs. time). The figure shows that the release profile of Ldopa can be manipulated precisely. By changing the composition of the coating polymers (in this case by changing the hypromellose to starch ratio) the rate of release of Ldopa can be increased or decreased. The formulations with a higher relative amount of hypromellose have a lower rate of Ldopa release than the formulations with a higher relative amount of starch. Besides the composition of the active ingredient coating layer, the application of an additional layer of coating (containing no Ldopa) can suitably be applied to lower the rate of release of Ldopa, as can be derived clearly from the graphs in FIG. 8 (i.e. by comparison of Levodopa 1 and levodopa 2 and by comparison of levodopa 3 and levodopa 4).

Effect of Damage and Self-Repair Capacity

The FDDSs were tested for their ability to maintain their floating capacity and the release profiles since many floating drug delivery systems of the prior art are known to be very vulnerable to damage resulting in impairment or total lack of their floating capacity (and hence gastric retention). A common cause for damage is inadvertant chewing movement by the subject taking the FDDS.

The FDDSs Levodopa 1-4 were damaged deliberately by squeezing them in a bench-vice, until cracks/ruptures developed visible to the naked eye. The damaged FDDSs were subjected to the same tests as the undamaged FDDS' (as described above) All damaged FDDSs remained afloat in the dissolution bath during the entire period of testing (12 hours). The release profiles of the damaged and undamaged FDDSs have been plotted in FIG. 9 (9_a_: L-dopa 1, 9_b_: L-dopa 2; 9_c_: L-dopa 3; and 9_d_: L-dopa 4). As can be inferred from these figures, the effect of damaging on the release profile is only marginal. At no time, the difference in released levodopa between damaged and undamaged formulation exceeded 8% and it was, in most cases below 5%.

To cause damage (cracking/rupture) visible to the naked eye, a significant force had to be applied, which required the use of the bench vice.

The invention claimed is:

1. A floating drug delivery system (FDDS), consisting of (i) a particle having a hollow, gas-filled core bordered by a wall of a polymer selected from the group of aqueous soluble or degradable polymers, and (ii) one or more coating layers surrounding said wall, said one or more coating layers each comprising an active ingredient and a coating material, wherein at least 75 wt. % of the coating material is a combination of hydroxypropyl methylcellulose (HPMC) and starch.

2. The floating drug delivery system according to claim 1, wherein the particle is a capsule.

3. The floating drug delivery system according to claim 1, wherein the active ingredient is not nicotinamide.

4. The floating drug delivery system according to claim 1, wherein the system maintains its release profile and floating properties when mechanically damaged or ruptured.

5. The floating drug delivery system according to claim 1, wherein the one or more coating layers comprises HPMC and starch in a ratio within the range of 8:1-1:1.

6. The floating drug delivery system according to claim 1, capable of remaining in the stomach for at least 6 hours and/or of releasing active ingredient to the stomach and proximal small intestine for at least 6 hours.

7. The floating drug delivery system according claim 1, having a density less than 0.95 g/cm3.

8. The floating drug delivery system according claim 1, having a density less than 0.8 g/cm3.

9. The floating drug delivery system according to claim 1, wherein the polymer that is aqueous soluble and/or degradable is gelatin.

10. The floating drug delivery system according to claim 1, wherein at least 80 wt. % of the coating material is a combination of hydroxypropyl methylcellulose (HPMC) and starch.

11. The floating drug delivery system according to claim 10, wherein at least 90 wt. % of the coating material is a combination of hydroxypropyl methylcellulose (HPMC) and starch.

12. The floating drug delivery system according to claim 1 or 5, comprising at least two active ingredient containing coating layers, wherein the at least two coating layers have distinct ratios of hydroxypropyl methylcellulose (HPMC) and starch.

13. The floating drug delivery system according to claim 12, wherein the outer layer comprises a larger amount of hydroxypropyl methylcellulose (HPMC), relative to starch, than the inner layer.

* * * * *